US009534217B2

(12) United States Patent
Soucaille et al.

(10) Patent No.: US 9,534,217 B2
(45) Date of Patent: Jan. 3, 2017

(54) METHOD OF CREATING A LIBRARY OF BACTERIAL CLONES WITH VARYING LEVELS OF GENE EXPRESSION

(75) Inventors: Philippe Soucaille, Deyme (FR); Marguerite A. Cervin, Palo Alto, CA (US); Fernando Valle, Palo Alto, CA (US)

(73) Assignee: DANISCO US IN., Palao Alto, CA (US)

( * ) Notice: Subject to any disclaimer, the term of this patent is extended or adjusted under 35 U.S.C. 154(b) by 386 days.

(21) Appl. No.: 13/155,290

(22) Filed: Jun. 7, 2011

(65) Prior Publication Data

US 2012/0015849 A1    Jan. 19, 2012

Related U.S. Application Data

(60) Continuation of application No. 11/942,503, filed on Nov. 19, 2007, now abandoned, which is a division of application No. 10/511,043, filed as application No. PCT/US03/12045 on Apr. 18, 2003, now abandoned.

(60) Provisional application No. 60/374,627, filed on Apr. 22, 2002.

(51) Int. Cl.
| | |
|---|---|
| *C12N 15/00* | (2006.01) |
| *C40B 40/06* | (2006.01) |
| *C40B 50/06* | (2006.01) |
| *C12P 19/34* | (2006.01) |
| *C12N 15/10* | (2006.01) |
| *C40B 40/08* | (2006.01) |

(52) U.S. Cl.
CPC ........... *C12N 15/1086* (2013.01); *C40B 40/08* (2013.01); *C40B 50/06* (2013.01)

(58) Field of Classification Search
None
See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,965,188 | A | 10/1990 | Mullis et al. |
| 5,888,732 | A | 3/1999 | Hartley et al. |
| 6,828,093 | B1 | 12/2004 | Elledge et al. |
| 7,670,823 | B1 | 3/2010 | Hartley et al. |

FOREIGN PATENT DOCUMENTS

| | | |
|---|---|---|
| WO | WO 94/25609 | 11/1994 |
| WO | WO 98/07846 | 2/1998 |
| WO | WO-01/55369 A1 | 8/2001 |

OTHER PUBLICATIONS

The Encode Project Consortium, "Identification and analysis of functional elements in 1% of the human genome by the Encode pilot project", Nature, 447 (Jun. 2007), 799-816.*
Stemmer et al 1995 Gene 164: 49-53.*
Casimiro et al 1997 Structure 5: 1407-1412.*
Abdel-Hamid, Ahmed M. et al., "Pyruvate oxidase contributes to the aerobic growth efficiency of *Escherichia coli*," Microbiology, 147:1483-1498 ( 2001).
Amann, Egon et al., "Vectors bearing a hybrid trp-lac promoter useful for regulated expression of cloned genes in *Escherichia coli*," Gene, 25:167-178 (1983).
Amore, Rene et al., "The fermentation of xylose—an analysis of the expression of Bacillus and Actinoplanes xylose isomerase genes in yeast," Applied Microbiology and Biotechnology, 30:351-357 (1989).
Burr, Tom et al., "DNA sequence elements located immediately upstream of the—10 hexamer in *Escherichia coli* promoters: a systematic study," Nucleic Acids Research, 28(9):1864-1870 (2000).
Chang, Shing et al., "High Frequency Transformation of Bacillus subtilis Protoplasts by Plasmid DNA," Molec. Gen. Genet., 168:111-115 (1979).
Cherepanov, Peter P. et al., "Gene disruption in *Escherichia coli*: $Tc^R$ and $Km^R$ cassettes with the option of Flp-catalyzed excision of the antibiotic-resistance determinant," Gene, 158:9-14 (1995).
Datsenko, Kirill A. et al., "One-step inactivation of chromosomal genes in *Escherichia coli* K-12 using PCR products," PNAS, 97(12):6640-6645 (2000).
DeHaseth, Pieter L. et al., "RNA Polymerase-Promoter Interactions: the Comings and Goings of RNA Polymerase," Journal of Bacteriology, 180(12):3019-3025 (1998).
Deuschle, Ulrich et al., "Promoters of *Escherichia coli*: a hierarchy of in vivo strength indicates alternate structures," The EMBO Journal, 5(11):2987-2994 (1986).
Devereux, Paul H. et al., "A Comprehensive Set of Sequence Analysis Programs for the VAX," 12(1):387-395 (1984).
Datsenko Kirill et al., "New tool for metabolic pathway engineering in *Escherichia coli*: One-step method to modulate expression of chromosomal genes," Proceedings of the National Academy of Sciences of USA, 97(12):6640-6645 (2000).
Ellermeir et al., "Construction of targeted single copy lac fusions using lambda Red and FLP-mediated site-specific recombination in bacteria," GENE, 290:(1-2):153-161 (2002).
Ferrari, Eugenio et al., Genetics, from *Bacillus*, ed. By Colin R. Harwood, Plenum Publishing Corporation, pp. 57-72 (1989).
Goeddel, David V., "Systems for Heterologous Gene Expression," Methods in Enzymology, 185:3-7, Academic Press (1990).
Gourse, Richard L. et al., "Ups and downs in bacterial transcription initiation: the role of the alpha subunit of RNA polymerase in promoter recognition," Molecular Microbiology, 37(4):687-695 (2000).
Hawley, Diane K. et al., Intermediates on the Pathway to Open-Complex Formation, from *Promoters, Structure and Function*, ed. by Rodriguez, R. L. et al., Praeger Special Studies, Praeger Scientific, pp. 55-68 (1982).

(Continued)

*Primary Examiner* — David Thomas
(74) *Attorney, Agent, or Firm* — Danisco US Inc.

(57) ABSTRACT

The present invention relates to a method of creating DNA libraries that include an artificial promoter library and/or a modified ribosome binding site library and transforming bacterial host cells with the library to obtain a population of bacterial clones having a range of expression levels for a chromosomal gene of interest.

30 Claims, 7 Drawing Sheets

(56) References Cited

OTHER PUBLICATIONS

Huang, L. C. et al., "A bacterial model system for chromosomal targeting," Nucleic Acids Research, 19(3):443-448 (1991).
Huffman Kenneth E. et al., "DNA-Sequence Asymmetry Directs the Alignment of Recombination Sites in the FLP Synaptic Complex," J. Mol. Biol., 286:1-13 (1999).
Israelsen, Hans et al., "Cloning and Partial Characterization of Regulated Promoters from *Lactococcus lactis* Tn917-*lac* Z Integrants with the New Promoter Probe Vector, pAK80," Applied and Environmental Microbiology, 61(7):2540-2547 (1995).
Jensen, Peter R. et al., "The Sequence of Spacers between the Consensus Sequences Modulates the Strength of Prokaryotic Promoters," Applied and Environmental Microbiology, 64(1):82-87 (1998).
Jensen, Peter R. et al., "Artificial Promoters for Metabolic Optimization," Biotechnology and Bioengineering, 582(2 & 3):191-195 (1998).
Khlebnikov, Artem et al., "Homogeneous expression of the $P_{BAD}$ promoter in *Escherichia coli* by constitutive expression of the low-affinity high-capacity AraE transporter," Microbiology, 147:3241-3247 (2001).
Martinez-Morales et al., "Chromosomal integration of heterologous DNA in *Scherichia coli* with precise removal of markers and replicons used during construction," J. of Bacteriology, 181:7143-7148 (1999).
Meynial-Salles et al., "New tool for metabolic pathway engineering in *Escherichia coli*: One-step method to modulate expression of chromosomal genes," Applied and Environmental Microbiology, 71:2140-2144 (2005).
McCracken, Andrea et al., "Efficiency of Transcription from Promoter Sequence Variants in Lactobacillus Is Both Strain and Context Dependent," Journal of Bacteriology, 181(20):6569-6572 (1999).
Needleman, Saul B. et al., "A General Method Applicable to the Search for Similarities in the Amino Acid Sequence of Two Proteins," J. Mol. Biol., 48:443-453 (1970).
Nunes-Duby, Simone E. et al., "Similarities and differences among 105 members of the Int family of site-specific recombinases," Nucleic Acids Research, 26(2):391-406 (1998).
Pearson, William R. et al., "Improved tools for biological sequence comparison," Proc. Natl. Acad. Sci. USA, 85:2444-2448 (1998).
Potter, Huntington, "Electroporation in Biology: Methods, Applications, and Instrumentation," Analytical Biochemistry, 174:361-373 (1988).

Repoila, F. et al., "Signal Transduction Cascade for Regulation of RpoS: Temperature Regulation of DsrA," Journal of Bacteriology, 183(13):4012-4023 (2001).
Russell, David R. et al., "Construction and analysis of in vivo activity of *E. coli* promoter hybrids and promoter mutants that alter the—35 to—10 spacing," Gene, 20:231-243 (1982).
Sizemore, Christine et al., "Quantitative analysis of Tn10 Tet repressor binding to a complete set of *tet* operator mutants," Nucleic Acids Research, 18(10):2875-2880 (1990).
Smith, Temple F., "Comparison of Biosequences," Advances in Applied Mathematics, 2:482-489 (1981).
Smith, Michael D. et al., "Protoplast Transformation in Coryneform Bacteria and Introduction of an α-Amylase Gene from Bacillus amyloliquefaciens into Brevibacterium lactofermentum," Applied and Environmental Microbiology, 51(3):634-639 (1986).
Sommer, Nicole et al., "T4 early promoter strength probed in vivo with unribosylated and ADP-ribosylated *Escherichia coli* RNA polymerase: a mutation analysis," Microbiology, 146:2643-2653 (2000).
Yu, et al., "An efficient recomination system for chromosome engineering in *Escherichia coli*," Proceedings of the National Academy of Sciences of USA, 97(11);5978-5983 (2000).
Zhu, Xu-Dong et al., "Homology Requirements for Ligation and Strand Exchange by the FLP Recombinase," 270(19):11646-11653 (1995).
Ausubel et al., eds., *Current Protocols in Molecular Biology*, vol. 1, John Wiley & Sons, Inc., Chapter 7, 1987.
Brock, T. D., in *Biotechnology : A Textbook of Industrial Microbiology*, $2^{nd}$. Ed., Sinauer Associates, Sunderland MA, 1989.
Gerhardt, P. et al., ed., *Manual of Methods of General Bacteriology*, American Society for Microbiology, Washington, D.C., 1981.
Hale and Markham, The Harper Collins Dictionary of Biology, Harper Perennial, New York, NY, 1991.
Innis et al., PCT Protocols : A Guide to Methods and Applications, Academic Press, San Diego, CA, 1990.
Miller, J. H. *A Short Course in Bacterial Genetics*, Cold Spring Harbor Laboratory Press, 1992.
Sambrook, J. et al., *Molecular Cloning : A Laboratory Manual*, Cold Spring Harbor Laboratory Press, 1989.
Singleton et al., *Dictionary of Microbiology and Molecular Biology*, ed. Ed., John Wiley and Sons, New York, NY, 1994.
PCT International Search Report for PCT/US03/12045, filed Apr. 18, 2003.

\* cited by examiner

FIGURE 4

```
        -50                              -7              +1                     +20
PH/E20  AACTGCAAAAATAGT TTGACA CCCTAGCCGATAGGCTT TAAGAT GTACCCAGTTGCGATGAGAGCGATAAC  (SEQ ID NO. 3)
PH207   TTTTAAAAAATTCAT TTGCTA AACGCTTCAAATTCTCG TATAAT ATACTTCATAAATTGATAAACAAAAA   (SEQ ID NO. 4)
PN25    TCATAAAAATTTAT  TTGCTT TCAGGAAAATTTTTCTG TATAAT AGATTCATAAATTGAGAGAGGAGTT    (SEQ ID NO. 5)
PG25    TGAAAAATAAAATTC TTGATA AAATTTTCCAATACTAT TATAAT ATTGTTATTAAAGAGGAGAAATTAAC   (SEQ ID NO. 6)
PJ5     ATATAAAAACCGTTA TTGACA CAGGTGGAAATTTAGAA TATACT GTTAGTAAACCTAATGGATCGACCTT   (SEQ ID NO. 7)
PA1     TTATCAAAAAGAGTA TTGACT TAAAGTCTAACCTATAG GATACT TACAGCCATCGAGAGGGACACGGCGA   (SEQ ID NO. 8)
PA2     CACGAAAAACAGGTA TTGACA ACATGAAGTAACATGCAGTAAGAT ACAAATCGCTAGGTAACACTAGACGC   (SEQ ID NO. 9)
PA3     GGTGAAACAAAACGG TTGACA CACTGAAGTAAACACGG TACGAT GTACCACATGAAACGACAGTGAGTCA   (SEQ ID NO. 10)
PL      TTATCTCTGGCGGTG TTGACA TAAAATACCACTGGCGGT GATACT GAGCACATCAGCAGGACGCACTGACC  (SEQ ID NO. 11)
Plac    TTAGGCACCCCAGGC TTTACA CTTTATGCTTCCGGCTCGGTATGTT GTGTGGAATTGTGAGCGGATAACAAT  (SEQ ID NO. 1)
PlacUV5 CTAGGCACCCCCAGG TTTACA CTTTATGCTTCCGGCTCGGTATAAT GTGTGGAATTGTGAGCGGATAACAAT  (SEQ ID NO. 12)
PtacI   TTCTGAAATGAGCTG TTGACA ATTAATCATCGGCTCG  TATAAT GTGTGGAATTGTGAGCGGATAACAAT   (SEQ ID NO. 2)
Pcon    AATTCACCGTCGTTG TTGACA TTTTTAAGCTTGGCGGT TATAAT GGTACCATAAGGAGGTGGATCCGGCA    (SEQ ID NO. 13)
Pbls    TTTTTTCTAAATACA TTCAAA TATGTATCCGCTCATGA GACAAT AACCCTGATAAATGCTTCAATAATAT   (SEQ ID NO. 14)
```

FIGURE 6 pLAC (SEQ ID NO. 18)
AGGC TTTACACTTTATGCTTCCGGCTCG TATGTT GTGTGGA ATGTGAGCGGATAACAATTTCACACAGGAAACAGCT ATGACC
        -35                                                  -10                                              RBS                    Start

1.6GI lacZ (SEQ ID NO. 19)
GCCC TTGACA ATGCCACATCCTGAGCA AATAAT TCAACCACT AATTGTGAGCGGATAACAATTTCACACAGGAAACAGCT ATGACC
        -35                                                  -10                                              RBS                    start

GI 1.6 (SEQ ID NO. 15)
GCCC TTGACA ATGCCACATCCTGAGCA AATAAT TCAACCACTAATTGTGAGCGGATAACA

1.5GI lacZ (SEQ ID NO. 20)
GCCC TTGACT ATGCCACATCCTGAGCA AATAAT TCAACCACT AATTGTGAGCGGATAACAATTTCACACAGGAAACAGCT ATGACC
        -35                                                  -10                                              RBS                    start

GI 1.5 SEQ ID NO. 16
GCCC TTGACT ATGCCACATCCTGAGCA AATAAT TCAACCACTAATTGTGAGCGGATAACA

1.20GI lacZ (SEQ ID NO. 21)
GCCC TTGACG ATGCCACATCCTGAGCA AATAAT TCAACCACT AATTGTGAGCGGATAACAATTTCACACAGGAAACAGCT ATGACC
        -35                                                  -10                                              RBS                    start

GI 1.2 (SEQ ID NO. 17)
GCCC TTGACG ATGCCACATCCTGAGCA AATAAT TCAACCACTAATTGTGAGCGGATAACA

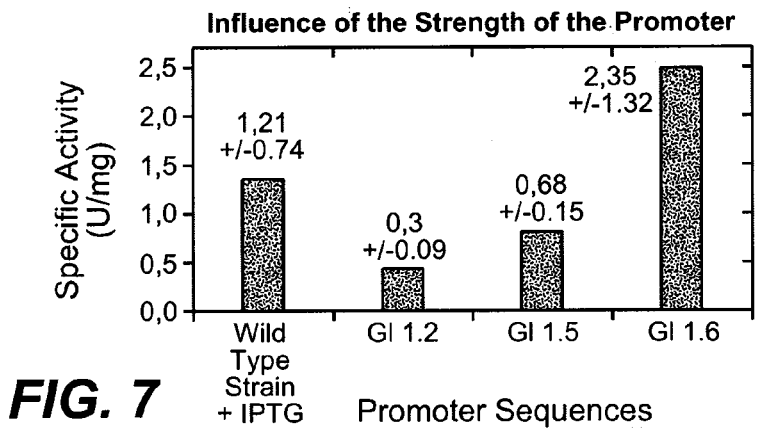
FIG. 7
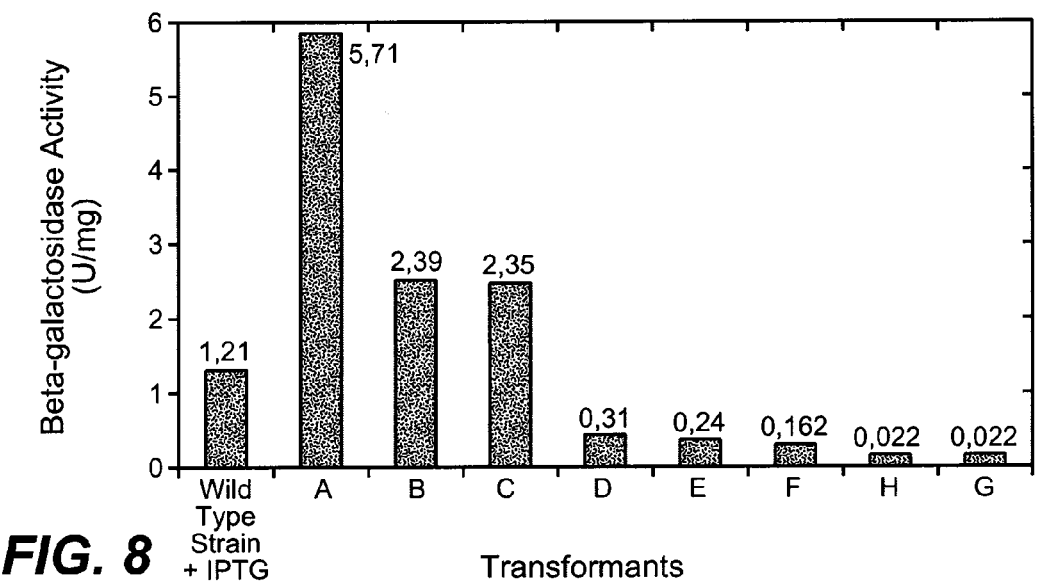
FIG. 8
| Transformants | Stabilizing Sequence | RBS Sequence | Specific Activity (U/mg) |
|---|---|---|---|
| mLac RNA 1 | GGTCGAG | AAGGAGGAAA | 5.71 |
| mLac RNA 2 | GGTGGAG | AAGGAGGAAA | 11.04 |
| mLac RNA 3 | CCTCGAG | AAGGAGGAAA | 18.44 |
| mLac RNA 4 | GGTGGAC | AAGGAGGAAA | 7.3 |
| mLac RNA 5 | GCTGGAC | AAGGAGGAAA | 4.11 |
| Wild-type Strain +IPTG | NO | AGGAAA | 1.21 |
FIG. 9

SEQUENCE LISTING

```
<160> NUMBER OF SEQ ID NOS: 75

<210> SEQ ID NO 1
<211> LENGTH: 70
<212> TYPE: DNA
<213> ORGANISM: Artificial Sequence
<220> FEATURE:
<223> OTHER INFORMATION: promoter

<400> SEQUENCE: 1
ttaggcaccc caggctttac actttatgct tccggctggt atgttgtgtg gaattgtgag      60
cgataacaat                                                            70

<210> SEQ ID NO 2
<211> LENGTH: 69
<212> TYPE: DNA
<213> ORGANISM: Artificial Sequence
<220> FEATURE:
<223> OTHER INFORMATION: promoter

<400> SEQUENCE: 2
```

```
ttctgaaatg agctgttgac aattaatcat cggctcgtat aatgtgtgga attgtgagcg    60
gataacaat                                                           69

<210> SEQ ID NO 3
<211> LENGTH: 70
<212> TYPE: DNA
<213> ORGANISM: Artificial Sequence
<220> FEATURE:
<223> OTHER INFORMATION: promoter

<400> SEQUENCE: 3
aactgcaaaa atagtttgac accctagccg ataggcttta agatgtaccc agttcgatga    60
gagcgataac                                                          70

<210> SEQ ID NO 4
<211> LENGTH: 70
<212> TYPE: DNA
<213> ORGANISM: Artificial Sequence
<220> FEATURE:
<223> OTHER INFORMATION: promoter

<400> SEQUENCE: 4
ttttaaaaaa ttcatttgct aaacgcttca aattctcgta taatatactt cataaattga    60
taaacaaaaa                                                          70

<210> SEQ ID NO 5
<211> LENGTH: 69
<212> TYPE: DNA
<213> ORGANISM: Artificial Sequence
<220> FEATURE:
<223> OTHER INFORMATION: promoter

<400> SEQUENCE: 5
tcataaaaaa tttatttgct ttcaggaaaa tttttctgta taatagattc ataaattgag    60
agaggagtt                                                           69

<210> SEQ ID NO 6
<211> LENGTH: 70
<212> TYPE: DNA
<213> ORGANISM: Artificial Sequence
<220> FEATURE:
<223> OTHER INFORMATION: promoter

<400> SEQUENCE: 6
tgaaaaataa aattcttgat aaaattttcc aatactatta taatattgtt attaaagagg    60
agaaattaac                                                          70

<210> SEQ ID NO 7
<211> LENGTH: 70
<212> TYPE: DNA
<213> ORGANISM: Artificial Sequence
<220> FEATURE:
<223> OTHER INFORMATION: promoter

<400> SEQUENCE: 7
atataaaaac cgttattgac acaggtggaa atttagaata tactgttagt aaacctaatg    60
gatcgacctt                                                          70

<210> SEQ ID NO 8
<211> LENGTH: 70
<212> TYPE: DNA
<213> ORGANISM: Artificial Sequence
```

```
<220> FEATURE:
<223> OTHER INFORMATION: promoter

<400> SEQUENCE: 8
ttatcaaaaa gagtattgac ttaaagtcta acctatagga tacttacagc catcgagagg      60
gacacggcga                                                              70

<210> SEQ ID NO 9
<211> LENGTH: 71
<212> TYPE: DNA
<213> ORGANISM: Artificial Sequence
<220> FEATURE:
<223> OTHER INFORMATION: promoter

<400> SEQUENCE: 9
cacgaaaaac aggtattgac aacatgaagt aacatgcagt aagatacaaa tcgctaggta      60
acactagacg c                                                            71

<210> SEQ ID NO 10
<211> LENGTH: 70
<212> TYPE: DNA
<213> ORGANISM: Artificial Sequence
<220> FEATURE:
<223> OTHER INFORMATION: promoter

<400> SEQUENCE: 10
ggtgaaacaa aacggttgac acactgaagt aaacacggta cgatgtacca catgaaacga      60
cagtgagtca                                                              70

<210> SEQ ID NO 11
<211> LENGTH: 70
<212> TYPE: DNA
<213> ORGANISM: Artificial Sequence
<220> FEATURE:
<223> OTHER INFORMATION: promoter

<400> SEQUENCE: 11
ttatctctgg cggtgttgac ataaatacca ctggcggtga tactgagcac atcagcagga      60
cgcactgacc                                                              70

<210> SEQ ID NO 12
<211> LENGTH: 71
<212> TYPE: DNA
<213> ORGANISM: Artificial Sequence
<220> FEATURE:
<223> OTHER INFORMATION: promoter

<400> SEQUENCE: 12
ctaggcaccc caggctttac actttatgct tccggctggt ataatgtgtg gaattgtgag      60
cggataacaa t                                                            71

<210> SEQ ID NO 13
<211> LENGTH: 70
<212> TYPE: DNA
<213> ORGANISM: Artificial Sequence
<220> FEATURE:
<223> OTHER INFORMATION: promoter

<400> SEQUENCE: 13
aattcaccgt cgttgttgac attttttaagc ttggcggtta taatggtacc ataaggaggt    60
ggatccggca                                                              70
```

```
<210> SEQ ID NO 14
<211> LENGTH: 70
<212> TYPE: DNA
<213> ORGANISM: Artificial Sequence
<220> FEATURE:
<223> OTHER INFORMATION: promoter

<400> SEQUENCE: 14
tttttcctaa atacattcaa atatgtatcc gctcatgaga caataaccct gataaatgct      60
tcaataatat                                                            70

<210> SEQ ID NO 15
<211> LENGTH: 60
<212> TYPE: DNA
<213> ORGANISM: Artificial Sequence
<220> FEATURE:
<223> OTHER INFORMATION: promoter

<400> SEQUENCE: 15
gcccttgaca atgccacatc ctgagcaaat aattcaacca ctaattgtga gcggataaca      60

<210> SEQ ID NO 16
<211> LENGTH: 60
<212> TYPE: DNA
<213> ORGANISM: Artificial Sequence
<220> FEATURE:
<223> OTHER INFORMATION: promoter

<400> SEQUENCE: 16
gcccttgact atgccacatc ctgagcaaat aattcaacca ctaattgtga gcggataaca      60

<210> SEQ ID NO 17
<211> LENGTH: 60
<212> TYPE: DNA
<213> ORGANISM: Artificial Sequence
<220> FEATURE:
<223> OTHER INFORMATION: promoter

<400> SEQUENCE: 17
gcccttgacg atgccacatc ctgagcaaat aattcaacca ctaattgtga gcggataaca      60

<210> SEQ ID NO 18
<211> LENGTH: 84
<212> TYPE: DNA
<213> ORGANISM: Artificial Sequence
<220> FEATURE:
<223> OTHER INFORMATION: promoter

<400> SEQUENCE: 18
aggctttaca ctttatgctt ccggctcgta tgttgtgtgg aattgtgagc ggataacaat      60
ttcacacagg aaacagctat gacc                                            84

<210> SEQ ID NO 19
<211> LENGTH: 84
<212> TYPE: DNA
<213> ORGANISM: Artificial Sequence
<220> FEATURE:
<223> OTHER INFORMATION: promoter

<400> SEQUENCE: 19
gcccttgaca atgccacatc ctgagcaaat aattcaacca ctaattgtga gcggataaca      60
atcacacagg aaacagctat gacc                                            84
```

```
<210> SEQ ID NO 20
<211> LENGTH: 86
<212> TYPE: DNA
<213> ORGANISM: Artificial Sequence
<220> FEATURE:
<223> OTHER INFORMATION: promoter

<400> SEQUENCE: 20
gcccttgact atgccacatc ctgagcaaat aattcaacca ctaattgtga gcggataaca    60
atttcacaca ggaaacagct atgacc                                        86

<210> SEQ ID NO 21
<211> LENGTH: 86
<212> TYPE: DNA
<213> ORGANISM: Artificial Sequence
<220> FEATURE:
<223> OTHER INFORMATION: promoter

<400> SEQUENCE: 21
gcccttgacg atgccacatc ctgagcaaat aattcaacca ctaattgtga gcggataaca    60
atttcacaca ggaaacagct atgacc                                        86

<210> SEQ ID NO 22
<211> LENGTH: 19
<212> TYPE: DNA
<213> ORGANISM: Artificial Sequence
<220> FEATURE:
<223> OTHER INFORMATION: recombinant clone

<400> SEQUENCE: 22
caaggaggaa acagctatg                                                19

<210> SEQ ID NO 23
<211> LENGTH: 19
<212> TYPE: DNA
<213> ORGANISM: Artificial Sequence
<220> FEATURE:
<223> OTHER INFORMATION: recombinant clone

<400> SEQUENCE: 23
caagaaggaa acagctatg                                                19

<210> SEQ ID NO 24
<211> LENGTH: 19
<212> TYPE: DNA
<213> ORGANISM: Artificial Sequence
<220> FEATURE:
<223> OTHER INFORMATION: recombinant clone

<400> SEQUENCE: 24
cacacaggaa acagctatg                                                19

<210> SEQ ID NO 25
<211> LENGTH: 19
<212> TYPE: DNA
<213> ORGANISM: Artificial Sequence
<220> FEATURE:
<223> OTHER INFORMATION: recombinant clone

<400> SEQUENCE: 25
ctcacaggag acagctatg                                                19

<210> SEQ ID NO 26
<211> LENGTH: 19
<212> TYPE: DNA
```

```
<213> ORGANISM: Artificial Sequence
<220> FEATURE:
<223> OTHER INFORMATION: recombinant clone

<400> SEQUENCE: 26
ctcacaggaa acagctatg                                                19

<210> SEQ ID NO 27
<211> LENGTH: 19
<212> TYPE: DNA
<213> ORGANISM: Artificial Sequence
<220> FEATURE:
<223> OTHER INFORMATION: recombinant clone

<400> SEQUENCE: 27
cacacagaaa acagctatg                                                19

<210> SEQ ID NO 28
<211> LENGTH: 19
<212> TYPE: DNA
<213> ORGANISM: Artificial Sequence
<220> FEATURE:
<223> OTHER INFORMATION: recombinant clone

<400> SEQUENCE: 28
ctcacagaga acagctatg                                                19

<210> SEQ ID NO 29
<211> LENGTH: 19
<212> TYPE: DNA
<213> ORGANISM: Artificial Sequence
<220> FEATURE:
<223> OTHER INFORMATION: recombinant clone

<400> SEQUENCE: 29
ctcacagaaa acagctatg                                                19

<210> SEQ ID NO 30
<211> LENGTH: 6
<212> TYPE: RNA
<213> ORGANISM: Artificial Sequence
<220> FEATURE:
<223> OTHER INFORMATION: ribosome binding site

<400> SEQUENCE: 30 aggaaa                                                               6

<210> SEQ ID NO 31
<211> LENGTH: 6
<212> TYPE: RNA
<213> ORGANISM: Artificial Sequence
<220> FEATURE:
<223> OTHER INFORMATION: ribosome binding site

<400> SEQUENCE: 31 agaaaa                                                               6

<210> SEQ ID NO 32
<211> LENGTH: 6
<212> TYPE: RNA
<213> ORGANISM: Artificial Sequence
<220> FEATURE:
<223> OTHER INFORMATION: ribosome binding site

<400> SEQUENCE: 32 agaaga                                                               6
```

```
<210> SEQ ID NO 33
<211> LENGTH: 6
<212> TYPE: RNA
<213> ORGANISM: Artificial Sequence
<220> FEATURE:
<223> OTHER INFORMATION: ribosome binding site

<400> SEQUENCE: 33 aggaga                                                                     6

<210> SEQ ID NO 34
<211> LENGTH: 10
<212> TYPE: RNA
<213> ORGANISM: Artificial Sequence
<220> FEATURE:
<223> OTHER INFORMATION: ribosome binding site

<400> SEQUENCE: 34
aagaaggaaa                                                                10

<210> SEQ ID NO 35
<211> LENGTH: 8
<212> TYPE: RNA
<213> ORGANISM: Artificial Sequence
<220> FEATURE:
<223> OTHER INFORMATION: ribosome binding site

<400> SEQUENCE: 35 aaggaaaa                                                                   8

<210> SEQ ID NO 36
<211> LENGTH: 8
<212> TYPE: RNA
<213> ORGANISM: Artificial Sequence
<220> FEATURE:
<223> OTHER INFORMATION: ribosome binding site

<400> SEQUENCE: 36 aaggaaag                                                                   8

<210> SEQ ID NO 37
<211> LENGTH: 8
<212> TYPE: RNA
<213> ORGANISM: Artificial Sequence
<220> FEATURE:
<223> OTHER INFORMATION: ribosome binding site

<400> SEQUENCE: 37 aaggaaau                                                                   8

<210> SEQ ID NO 38
<211> LENGTH: 9
<212> TYPE: RNA
<213> ORGANISM: Artificial Sequence
<220> FEATURE:
<223> OTHER INFORMATION: ribosome binding site

<400> SEQUENCE: 38 aaggaaaaa                                                                  9

<210> SEQ ID NO 39
<211> LENGTH: 9
<212> TYPE: RNA
<213> ORGANISM: Artificial Sequence
<220> FEATURE:
```

```
<223> OTHER INFORMATION: ribosome binding site

<400> SEQUENCE: 39 aaggaaaag                                                                  9

<210> SEQ ID NO 40
<211> LENGTH: 9
<212> TYPE: RNA
<213> ORGANISM: Artificial Sequence
<220> FEATURE:
<223> OTHER INFORMATION: ribosome binding site

<400> SEQUENCE: 40 aaggaaaau                                                                  9

<210> SEQ ID NO 41
<211> LENGTH: 10
<212> TYPE: RNA
<213> ORGANISM: Artificial Sequence
<220> FEATURE:
<223> OTHER INFORMATION: ribosome binding site

<400> SEQUENCE: 41
aaggaaaaaa                                                                10

<210> SEQ ID NO 42
<211> LENGTH: 10
<212> TYPE: RNA
<213> ORGANISM: Artificial Sequence
<220> FEATURE:
<223> OTHER INFORMATION: ribosome binding site

<400> SEQUENCE: 42
aaggaaaaag                                                                10

<210> SEQ ID NO 43
<211> LENGTH: 10
<212> TYPE: RNA
<213> ORGANISM: Artificial Sequence
<220> FEATURE:
<223> OTHER INFORMATION: ribosome binding site

<400> SEQUENCE: 43
aaggaaaaau                                                                10

<210> SEQ ID NO 44
<211> LENGTH: 11
<212> TYPE: RNA
<213> ORGANISM: Artificial Sequence
<220> FEATURE:
<223> OTHER INFORMATION: ribosome binding site

<400> SEQUENCE: 44
aaggaaaaaa a                                                              11

<210> SEQ ID NO 45
<211> LENGTH: 11
<212> TYPE: RNA
<213> ORGANISM: Artificial Sequence
<220> FEATURE:
<223> OTHER INFORMATION: ribosome binding site

<400> SEQUENCE: 45
aaggaaaaaa g                                                              11
```

```
<210> SEQ ID NO 46
<211> LENGTH: 11
<212> TYPE: RNA
<213> ORGANISM: Artificial Sequence
<220> FEATURE:
<223> OTHER INFORMATION: ribosome binding site

<400> SEQUENCE: 46
aaggaaaaaa u                                                              11

<210> SEQ ID NO 47
<211> LENGTH: 12
<212> TYPE: RNA
<213> ORGANISM: Artificial Sequence
<220> FEATURE:
<223> OTHER INFORMATION: ribosome binding site

<400> SEQUENCE: 47
aaggaaaaaa aa                                                             12

<210> SEQ ID NO 48
<211> LENGTH: 12
<212> TYPE: RNA
<213> ORGANISM: Artificial Sequence
<220> FEATURE:
<223> OTHER INFORMATION: ribosome binding site

<400> SEQUENCE: 48
aaggaaaaaa ag                                                             12

<210> SEQ ID NO 49
<211> LENGTH: 12
<212> TYPE: RNA
<213> ORGANISM: Artificial Sequence
<220> FEATURE:
<223> OTHER INFORMATION: ribosome binding site

<400> SEQUENCE: 49
aaggaaaaaa au                                                             12

<210> SEQ ID NO 50
<211> LENGTH: 13
<212> TYPE: RNA
<213> ORGANISM: Artificial Sequence
<220> FEATURE:
<223> OTHER INFORMATION: ribosome binding site

<400> SEQUENCE: 50
aaggaaaaaa aaa                                                            13

<210> SEQ ID NO 51
<211> LENGTH: 13
<212> TYPE: RNA
<213> ORGANISM: Artificial Sequence
<220> FEATURE:
<223> OTHER INFORMATION: ribosome binding site

<400> SEQUENCE: 51
aaggaaaaaa aag                                                            13

<210> SEQ ID NO 52
<211> LENGTH: 13
<212> TYPE: RNA
<213> ORGANISM: Artificial Sequence
<220> FEATURE:
<223> OTHER INFORMATION: ribosome binding site
```

<400> SEQUENCE: 52
aaggaaaaaa aau                                                          13

<210> SEQ ID NO 53
<211> LENGTH: 14
<212> TYPE: RNA
<213> ORGANISM: Artificial Sequence
<220> FEATURE:
<223> OTHER INFORMATION: ribosome binding site

<400> SEQUENCE: 53
aaggaaaaaa aaaa                                                         14

<210> SEQ ID NO 54
<211> LENGTH: 14
<212> TYPE: RNA
<213> ORGANISM: Artificial Sequence
<220> FEATURE:
<223> OTHER INFORMATION: ribosome binding site

<400> SEQUENCE: 54
aaggaaaaaa aaag                                                         14

<210> SEQ ID NO 55
<211> LENGTH: 10
<212> TYPE: RNA
<213> ORGANISM: Artificial Sequence
<220> FEATURE:
<223> OTHER INFORMATION: ribosome binding site

<400> SEQUENCE: 55
aaggaggaaa                                                              10

<210> SEQ ID NO 56
<211> LENGTH: 14
<212> TYPE: RNA
<213> ORGANISM: Artificial Sequence
<220> FEATURE:
<223> OTHER INFORMATION: ribosome binding site

<400> SEQUENCE: 56
aaggaaaaaa aaau                                                         14

<210> SEQ ID NO 57
<211> LENGTH: 100
<212> TYPE: DNA
<213> ORGANISM: Artificial Sequence
<220> FEATURE:
<223> OTHER INFORMATION: synthetic oligonucleotide

<400> SEQUENCE: 57
tagctgtttc ctgtgtgaaa ttgttatccg ctcacaatta gtggttgaat tatttgctca       60
ggatgtggca thgtcaaggg catatgaata tcctccttag                            100

<210> SEQ ID NO 58
<211> LENGTH: 100
<212> TYPE: DNA
<213> ORGANISM: Artificial Sequence
<220> FEATURE:
<223> OTHER INFORMATION: synthetic oligonucleotide

<400> SEQUENCE: 58
gtgaaaccag taacgttata cgatgtcgca gagtatgccg gtgtctctta tcagaccgtt       60
tcccgcgtgg tgaaccaggg tgtaggctgg agctgcttcg                            100

```
<210> SEQ ID NO 59
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 59
ggctgcgcaa ctgttgggaa                                                    20

<210> SEQ ID NO 60
<211> LENGTH: 22
<212> TYPE: DNA
<213> ORGANISM: Artificial Sequence
<220> FEATURE:
<223> OTHER INFORMATION: synthetic oligonucleotide

<400> SEQUENCE: 60
cattgaacag gcagcggaaa ag                                                 22

<210> SEQ ID NO 61
<211> LENGTH: 100
<212> TYPE: DNA
<213> ORGANISM: Artificial Sequence
<220> FEATURE:
<223> OTHER INFORMATION: synthetic oligonucleotide

<400> SEQUENCE: 61
cagggttttc ccagtcacga cgttgtaaaa cgacggccag tgaatccgta atcatggtca        60
tagctgtyty ctbykwgaaa ttgttatccg ctcacaatta                             100

<210> SEQ ID NO 62
<211> LENGTH: 103
<212> TYPE: DNA
<213> ORGANISM: Artificial Sequence
<220> FEATURE:
<223> OTHER INFORMATION: synthetic oligonucleotide

<400> SEQUENCE: 62
cgacggccag tgaatccgta atcatggtca tagctgtttc ctccttcgtc aacaatatct        60
cactcgagat aastcgasst agtggttgaa ttatttgctc agg                         103

<210> SEQ ID NO 63
<211> LENGTH: 33
<212> TYPE: DNA
<213> ORGANISM: Artificial Sequence
<220> FEATURE:
<223> OTHER INFORMATION: mRNA stabilizing sequence

<400> SEQUENCE: 63
ggtcgagtta tctcgagtga gatattgttg acg                                     33

<210> SEQ ID NO 64
<211> LENGTH: 33
<212> TYPE: DNA
<213> ORGANISM: Artificial Sequence
<220> FEATURE:
<223> OTHER INFORMATION: mRNA stabilizing sequence

<400> SEQUENCE: 64
ggtggactta tctcgagtga gatattgttg acg                                     33

<210> SEQ ID NO 65
```

<211> LENGTH: 33
<212> TYPE: DNA
<213> ORGANISM: Artificial Sequence
<220> FEATURE:
<223> OTHER INFORMATION: mRNA stabilizing sequence

<400> SEQUENCE: 65
cctcgagtta tctcgagtga gatattgttg acg         33

<210> SEQ ID NO 66
<211> LENGTH: 33
<212> TYPE: DNA
<213> ORGANISM: Artificial Sequence
<220> FEATURE:
<223> OTHER INFORMATION: mRNA stabilizing sequence

<400> SEQUENCE: 66
gctcgagtta tctcgagtga gatattgttg acg         33

<210> SEQ ID NO 67
<211> LENGTH: 33
<212> TYPE: DNA
<213> ORGANISM: Artificial Sequence
<220> FEATURE:
<223> OTHER INFORMATION: mRNA stabilizing sequence

<400> SEQUENCE: 67
cgtcgagtta tctcgagtga gatattgttg acg         33

<210> SEQ ID NO 68
<211> LENGTH: 33
<212> TYPE: DNA
<213> ORGANISM: Artificial Sequence
<220> FEATURE:
<223> OTHER INFORMATION: mRNA stabilizing sequence

<400> SEQUENCE: 68
ggtggagtta tctcgagtga gatattgttg acg         33

<210> SEQ ID NO 69
<211> LENGTH: 33
<212> TYPE: DNA
<213> ORGANISM: Artificial Sequence
<220> FEATURE:
<223> OTHER INFORMATION: mRNA stabilizing sequence

<400> SEQUENCE: 69
gctggactta tctcgagtga gatattgttg acg         33

<210> SEQ ID NO 70
<211> LENGTH: 99
<212> TYPE: DNA
<213> ORGANISM: Artificial Sequence
<220> FEATURE:
<223> OTHER INFORMATION: synthetic oligonucleotide

<400> SEQUENCE: 70
tagctgtttc ctgtgtgaaa ttgttatccg ctcacaatta gtggttgaat tatttgctca         60
ggatgtggca tgtcaagggc atatgaatat cctccttag                               99

<210> SEQ ID NO 71
<211> LENGTH: 100
<212> TYPE: DNA
<213> ORGANISM: Artificial Sequence
<220> FEATURE:
<223> OTHER INFORMATION: synthetic oligonucleotide

```
<400> SEQUENCE: 71
cagggttttc ccagtcacga cgttgtaaaa cgacggccag tgaatccgta atcatggtca    60
hagctgtyty ctbykwgaaa ttgttatccg ctcacaatta                         100

<210> SEQ ID NO 72
<211> LENGTH: 10
<212> TYPE: DNA
<213> ORGANISM: Artificial Sequence
<220> FEATURE:
<223> OTHER INFORMATION: recombinant clone

<400> SEQUENCE: 72
tcacaggaga                                                          10

<210> SEQ ID NO 73
<211> LENGTH: 9
<212> TYPE: DNA
<213> ORGANISM: Artificial Sequence
<220> FEATURE:
<223> OTHER INFORMATION: recombinant clone

<400> SEQUENCE: 73 aaggaggaa                                                            9

<210> SEQ ID NO 74
<211> LENGTH: 10
<212> TYPE: DNA
<213> ORGANISM: Artificial Sequence
<220> FEATURE:
<223> OTHER INFORMATION: recombinant clone

<400> SEQUENCE: 74
acacaggaaa                                                          10

<210> SEQ ID NO 75
<211> LENGTH: 10
<212> TYPE: DNA
<213> ORGANISM: Artificial Sequence
<220> FEATURE:
<223> OTHER INFORMATION: recombinant clone

<400> SEQUENCE: 75
acacagaaga                                                          10
```

METHOD OF CREATING A LIBRARY OF BACTERIAL CLONES WITH VARYING LEVELS OF GENE EXPRESSION

CROSS-REFERENCE TO RELATED APPLICATIONS

The present application is a continuation of U.S. patent application Ser. No. 11/942,503, filed Nov. 19, 2007, which is a divisional of U.S. patent application Ser. No. 10/511,043, filed Jun. 15, 2005, which is the National Phase filing under 35 U.S.C. §371 of International Application No. PCT/US03/12045, filed Apr. 18, 2003, which claims the benefit of U.S. Provisional Application No. 60/374,627, filed Apr. 22, 2002. The specifications of each of these applications are hereby incorporated by reference in their entirety.

FIELD OF INVENTION

The present invention relates to the genetic modification of bacterial cells. Particularly to a method of creating DNA libraries that comprise a library of artificial promoters and/or a library of modified regulatory regions, and the use of the libraries to replace precursor promoters and regulatory regions in bacterial host cells resulting in a library of bacterial clones having a range of expression levels of a gene of interest.

BACKGROUND OF THE INVENTION

For many years microorganisms have been exploited in industrial applications for the production of valuable commercial products, such as industrial enzymes, hormones and antibodies. Despite the fact that recombinant DNA technology has been used in an attempt to increase the productivity of these microorganisms, the use of metabolic genetic engineering to improve strain performance, particularly in industrial fermentations has been disappointing.

A common strategy used to increase microbial strain performance is to alter gene expression, and a number of means have been used to achieve this end. One approach includes the cloning of a heterologous or a homologous gene in a multi-copy plasmid in a selected host strain. Another approach concerns altering chromosomal gene expression. This has been accomplished by various methods some of which include: (1) site-specific mutations, deletions or insertions at a predetermined region of a chromosome; (2) reliance on transposons to insert DNA randomly into chromosomes and (3) altering of native regulatory regions of a gene at its chromosomal location. The alteration of regulatory regions can be accomplished for example, by changing promoter strength or by using regulatable promoters which are influenced by inducer concentration. Reference is made to Jensen and Hammer, (1998) *Biotechnology and Bioengineering* 58:193-195; Jensen and Hammer (1998) *Appl. Environ. Microbio.* 64:82-85; and Khlebnikov et al. (2001) *Microbiol.* 147:3241. Other techniques used to replace regulatory regions of chromosomal gene have been disclosed in Abdel-Hamid et al. (2001) *Microbiol.* 147:1483-1498 and Repoila and Gottesman (2001) *J. Bacteriol.* 183:4012-4023.

With respect to optimizing metabolic pathway engineering in a selected host, the above-mentioned approaches have had limited success and each approach has certain disadvantages. Research has shown the expression level of a genetically modified gene on a plasmid is not necessarily correlated with the level of expression of the same modified gene located in the chromosome (See Khlebnikov et al. (2001) *Microbiol.* 147:3241 and McCraken and Timms (1999) *J. Bacteriol.* 18:6569).

Moreover, the effect of increasing expression of one gene in a metabolic pathway may only have a marginal effect on the flux through that metabolic pathway. This may be true even if the gene being manipulated codes for an enzyme in a rate-limiting step because control of a metabolic pathway may be distributed over a number of enzymes. Therefore, while a gene has been engineered to achieve a high level of expression, for example a 10 to 100 fold increase in expression, the overall performance of the engineered microorganism in a bioreactor may decrease. The decrease could be due to the balance of other factors involved in the metabolic pathway or the depletion of other substances necessary for optimum cell growth.

The above problem is addressed in part by Jensen and Hammer (WO 98/07846). The disclosure of WO98/07846 describes the construction of a set of constitutive promoters that provide different levels of gene expression. Specifically, artificial promoter libraries are constructed comprising variants of a regulatory region that includes a −35 consensus box, a −10 consensus box and a spacer (linker) region that lies between these consensus regions. However, one of the drawbacks of the method described in WO 98/07846 is the extensive screening (in terms of time and numbers of steps), which would be required to create a library of clones with different levels of gene expression. It is also disclosed in the reference that the modulation of promoter strength, by a few base-pair changes in the consensus sequences or by changes in the linker sequence, would result in a large impact in promoter strength, and therefore, it would not be feasible to achieve small steps on promoter strength modulation.

Therefore, a need still exists in the area of metabolic pathway engineering to develop a quick and efficient means of determining the optimum expression of a gene of interest in a metabolic pathway which in turn results in an optimization of strain performance for a desired product. The present method satisfies this need by providing a method to characterize small changes in gene expression level and hence allowing for the selection of a cell providing an optimum level of expression.

SUMMARY OF THE INVENTION

In one aspect the invention relates to a method of creating a library of artificial promoters comprising a) obtaining an insertion DNA cassette, which comprises, a first recombinase site, a second recombinase site and a selective marker gene located between the first and the second recombinase sites; b) obtaining a first oligonucleotide which comprises, i) a first nucleic acid fragment homologous to an upstream region of a chromosomal gene of interest, and ii) a second nucleic acid fragment homologous to a 5' end of the insertion DNA cassette; c) obtaining a second oligonucleotide which comprises, i) a third nucleic acid fragment homologous to a 3' end of said insertion DNA cassette, ii) a precursor promoter comprising a −35 consensus region (−35 to −30), a linker sequence and a −10 consensus region (−12 to −7), wherein the linker sequence comprises between 14-20 nucleotides and is flanked by the −35 region and the −10 region, wherein said precursor promoter has been modified to include at least one modified nucleotide position of the precursor promoter and wherein the −35 region and the −10 region each include between 4 to 6 conserved nucleotides of the promoter, and iii) a fourth nucleic acid fragment homologous to a downstream region of the transcription start site of the promoter; and d) mixing the first oligonucleotide and the second oligonucleotide in an amplification reaction with the insertion DNA cassette to obtain a library of double stranded amplified products comprising artificial promoters. In one embodiment, the method further comprises purifying the amplified products. In another embodiment, the amplification step is by PCR. In another embodiment, the precursor promoter is selected from the group consisting of $P_{trc}$ (SEQ ID NO 2); $P_{D/E20}$ ((SEQ ID NO. 4); $P_{H207}$ (SEQ ID NO. 3); $PN_{N25}$ (SEQ ID NO. 5); $P_{G25}$ (SEQ ID NO.6); $P_{J5}$ (SEQ ID NO.7); $P_{A1}$ (SEQ ID NO. 8); $P_{A2}$ (SEQ ID NO. 9); $P_{A3}$ (SEQ ID NO. 10); $P_{lac}$ (SEQ ID NO. 1); $P_{lacUV5}$ (SEQ ID NO. 12); $P_{CON}$ (SEQ ID NO.4); $P_{GI}$ (SEQ ID NO. 15) and $P_{bis}$(SEQ ID NO. 14). In a further embodiment the artificial promoter library includes the promoters designated by SEQ ID NO. 15, SEQ ID NO. 16 and SEQ ID NO. 17. In a further embodiment the invention includes the artificial promoter library produced according to the above method.

In a second aspect, the invention relates to a method of creating a library of ribosome binding sites (RBS) comprising a) obtaining an insertion DNA cassette, which comprises, a first recombinase site, a second recombinase site and a selective marker gene located between the first and the second recombinase sites; b) obtaining a first oligonucleotide which comprises, i) a first nucleic acid fragment homologous to an upstream region of a chromosomal gene of interest, and ii) a second nucleic acid fragment homologous to a 5' end of the insertion DNA cassette; c) obtaining a second oligonucleotide which comprises, i) a third nucleic acid fragment homologous to a 3' end of said insertion DNA cassette, ii) a precursor promoter comprising a −35 consensus region (−35 to −30), a linker sequence and a −10 consensus region (−12 to −7), wherein the linker sequence comprises between 14-20 nucleotides and is flanked by the −35 region and the −10 region, wherein said precursor promoter has been modified to include at least one modified nucleotide position of the precursor promoter and wherein the −35 region and the −10 region each include between 4 to 6 conserved nucleotides of the promoter, and iii) a fourth nucleic acid fragment homologous to a downstream region of the transcription start site of the promoter; and d) mixing the first oligonucleotide and the second oligonucleotide in an amplification reaction with the insertion DNA cassette to obtain a library of double stranded amplified products comprising artificial promoters and e) obtaining a third oligonucleotide which comprises, i) a fifth nucleic acid fragment homologous to the 5' end of said chromosomal gene of interest, ii) a modified ribosome binding site of the gene of interest, said ribosome binding site including at least one modified nucleotide, and iii) a sixth nucleic acid fragment homologous to a downstream region of the −10 region of the second oligonucleotide; and e) mixing the PCR products of step d) with the third oligonucleotide of step e) and the first oligonucleotide og step b) in a PCR reaction to obtain PCR products comprising artificial promoters with modified ribosome binding sites. In an embodiment the ribosome binding site is selected from the group consisting of AGGAAA, (SEQ ID NO. 30), AGAAAA (SEQ ID NO. 31), AGAAGA (SEQ ID NO. 32), AGGAGA (SEQ ID NO. 33), AAGAAGGAAA (SEQ ID NO. 34), AAGGAAAA (SEQ ID NO. 35), AAGGAAAG (SEQ ID NO. 36), AAGGAAAU (SEQ ID NO. 37), AAGGAAAAA (SEQ ID NO. 38), AAGGAAAAG (SEQ ID NO. 39), AAGGAAAAU (SEQ ID NO. 40), AAGGAAAAAA (SEQ ID NO. 41), AAGGAAAAAG (SEQ ID NO. 42), AAGGAAAAAU (SEQ ID NO. 43), AAGGAAAAAAA (SEQ ID NO. 44), AAGGAAAAAAG (SEQ ID NO. 45), AAGGAAAAAAU (SEQ ID NO. 46), AAGGAAAAAAAA (SEQ ID NO. 47), AAGGAAAAAAAG (SEQ ID NO. 48), AAGGAAAAAAAU (SEQ ID NO. 49), AAGGAAAAAAAAA (SEQ ID NO. 50), AAGGAAAAAAAAG (SEQ ID NO. 51), AAGGAAAAAAAAU (SEQ ID NO. 52), AAGGAAAAAAAAAA (SEQ ID NO. 53), AAGGAAAAAAAAAG (SEQ ID NO. 54), AAGGAGGAAA (SEQ ID NO. 55), and AAGGAAAAAAAAAU (SEQ ID NO. 56). In a further embodiment the invention includes the artificial promoter library produced according to the above method.

In a third aspect, the invention relates to an artificial promoter library comprising a mixture of double stranded polynucleotides which include in sequential order: a) a nucleic acid fragment homologous to an upstream region of a chromosomal gene of interest, b) a first recombinase site, c) a nucleic acid sequence encoding an antimicrobial resistance gene, d) a second recombinase site, e) two consensus regions of a promoter and a linker sequence, wherein the first consensus region comprises a −35 region, the second consensus region comprises a −10 region and the linker sequence comprises at least 14-20 nucleotides and is flanked by the first consensus region and wherein the second consensus region and the −35 region and the −10 region each include between 4 -6 conserved nucleotides of corresponding consensus regions of the promoter, and f) a nucleic acid fragment homologous to the downstream region of the +1 transcription start site of the promoter. In one embodiment the promoter library of the double stranded polynucleotides will also include a modified start codon, wherein the modified start codon sequence is located between the −10 region and the nucleic acid sequence homologous to the downstream region of the +1 transcription start site. In another embodiment the promoter library of double stranded polynucleotides further include a stabilizing mRNA nucleic acid sequence, wherein the stabilizing mRNA sequence is located between the −10 region and the nucleic acid sequence homologous to the downstream region of the +1 transcription start site.

In a fourth aspect, the invention relates to a method of modifying a promoter in selected host cells comprising obtaining a library of PCR products comprising artificial promoters, RBS, start codons or stablizing mRNA sequences or combinations thereof according to the invention; b) transforming bacterial host cells with the PCR library, wherein the PCR products comprising the artificial promoters are integrated into the bacterial host cells by homologous recombination; c) growing the transformed bacteria cells; d) selecting the transformed bacterial cells comprising the artificial promoters. In certain embodiments the bacterial host cell is selected from the group consisting of *E. coli*, *Pantoea* sp. and *Bacillus* sp.

In a fifth aspect, the invention relates to a method of creating a library of bacterial cells having a range of expression levels of a chromosomal gene of interest comprising, a) obtaining a library of PCR products comprising artificial promoters according to the invention; b) transforming bacterial host cells with the PCR products, wherein the PCR products comprising the artificial promoters are integrated into bacterial host cells by homologous recombination to produce transformed bacterial cells; c) growing the transformed bacteria cells; and d) obtaining a library of transformed bacterial cells wherein the library exhibits a range of expression levels of a chromosomal gene of interest. In one embodiment the method further comprises selecting transformed bacterial cells from the library. In a second embodiment the selected transformed cells will have a low level of expression of the gene of interest, and in another embodiment the selected transformed bacterial cells have a high level of expression of the gene of interest.

BRIEF DESCRIPTION OF THE DRAWINGS

FIG. 4 illustrates the sequences of various well-characterized promoters and includes approximately 50 base pair (bp) upstream of the transcription start site (+1), including the −35 consensus boxes, the linker sequences and the −10 consensus boxes. The promoters are aligned with respect to the first T of the −35 consensus box and the last T of the −10 consensus box. The conserved regions are indicated in bold. $P_{D/E20}$ is represented by SEQ ID NO. 3; $P_{H207}$ is represented by SEQ ID NO. 4; $P_{N25}$ is represented by SEQ ID NO. 5; $P_{G25}$ is represented by SEQ ID NO. 6; $P_{J5}$ is represented by SEQ ID NO. 7; $P_{41}$ is represented by SEQ ID NO. 8; $P_{42}$ is represented by SEQ ID NO. 9; $P_{43}$ is represented by SEQ ID NO. 10; $P_L$ is represented by SEQ ID NO. 11; $P_{lac}$ is represented by SEQ ID NO. 1; $P_{lacUV5}$ is represented by SEQ ID NO. 12; $P_{tacI}$ is represented by SEQ ID NO. 2; $P_{con}$ is represented by SEQ ID NO. 13; and $P_{bla}$ is represented by SEQ ID NO. 14.

FIG. 6 illustrates a library of promoters comprising three artificial promoters used to replace the lactose operon promoter Plac (SEQ ID NO. 18) and the lacI regulator. The library of promoters comprises three artificial glucose isomerase promoters: 1.6 GI lacZ (SEQ ID NO. 19) which includes the 1.6GI promoter (SEQ ID NO. 15); 1.5 GI lacZ (SEQ ID NO. 20) which includes the 1.5 GI promoter (SEQ ID NO. 16); and 1.2 GI lacZ (SEQ ID NO. 21) which includes the 1.2 GI promoter (SEQ ID NO. 17).

FIG. 7 illustrates the expression of the lacZ gene measured as specific activity of (β-galactosidase in a library of E. coli cells transformed with the library comprising 1.6 GI lacZ (SEQ ID NO. 19), 1.5 GI lacZ (SEQ ID NO. 20) and 1.2 GI lacZ (SEQ ID NO. 21).

FIG. 8 illustrates the expression of the lacZ gene with the 1.6GI promoter (SEQ ID NO. 19), wherein the ribosome binding site has been altered. Transformants are designated

Figure 1:
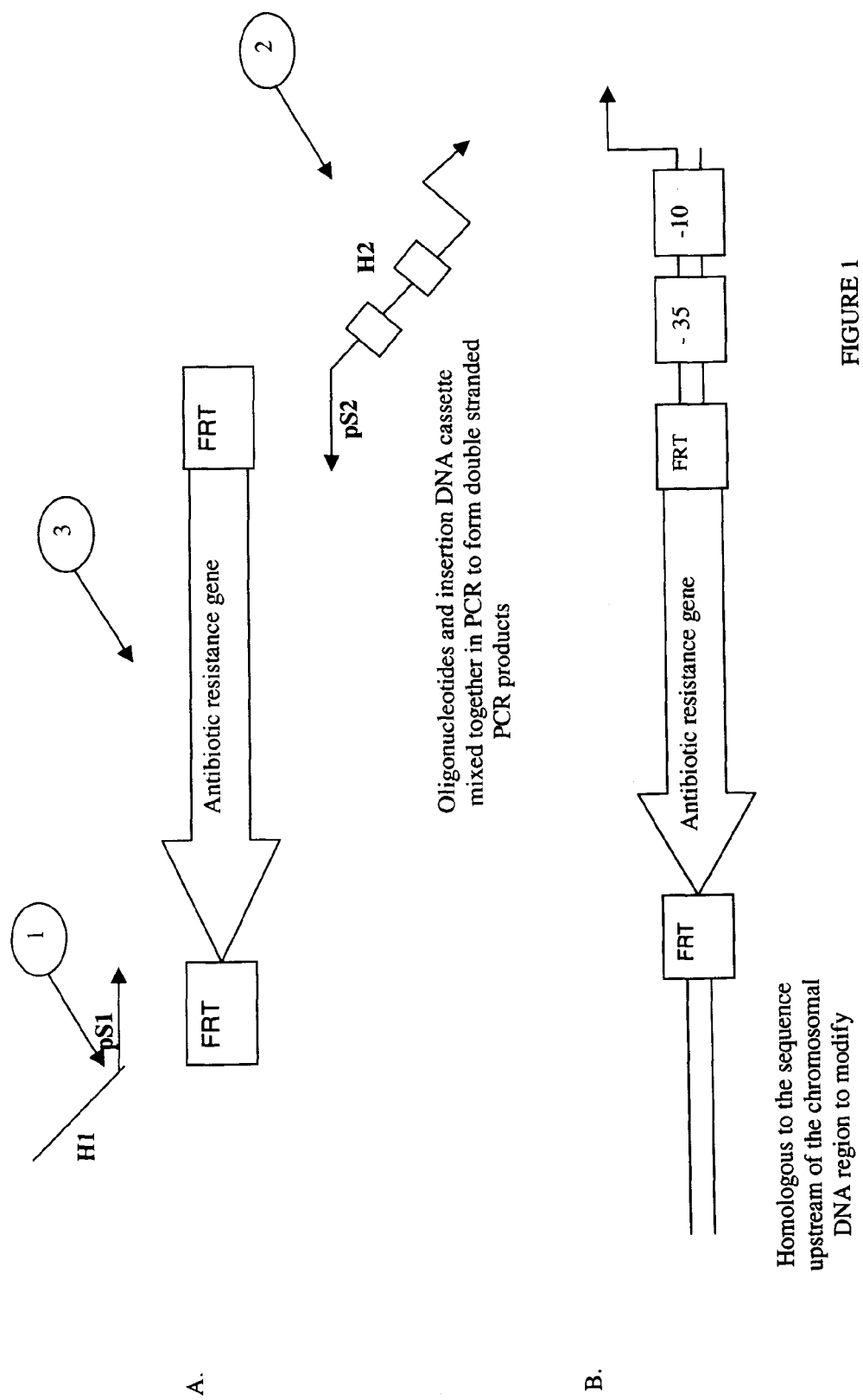
FIG. 1 illustrates a schematic representation of a method of creating an artificial promoter library and the double stranded PCR products obtained according to the method of the invention. Two oligonucleotides which are represented by numbers (1) and (2) and an insertion DNA cassette on a plasmid (3) are mixed together in a PCR reaction to form a mixture of double stranded PCR products. Oligonucleotide (1) includes nucleic acid sequences homologous to an upstream region of a chromosomal gene of interest (H1) and a primer site (PS1). The PS1 is homologous to the first end (5') of an insertion DNA cassette (3). Oligonucleotide (2) is degenerated and includes a primer site (PS2) and artificial promoter sequences (H2). The PS2 is homologous to the second end (3') of the insertion DNA cassette (3). The artificial promoter sequences (H2) comprise different modified −35 consensus regions, different modified linker regions, and different modified −10 consensus regions or combinations thereof. The insertion DNA construct (3) includes a selective marker, which is preferably an antibiotic resistant gene, flanked by two recombinase sites (FRT).
Figure 2:
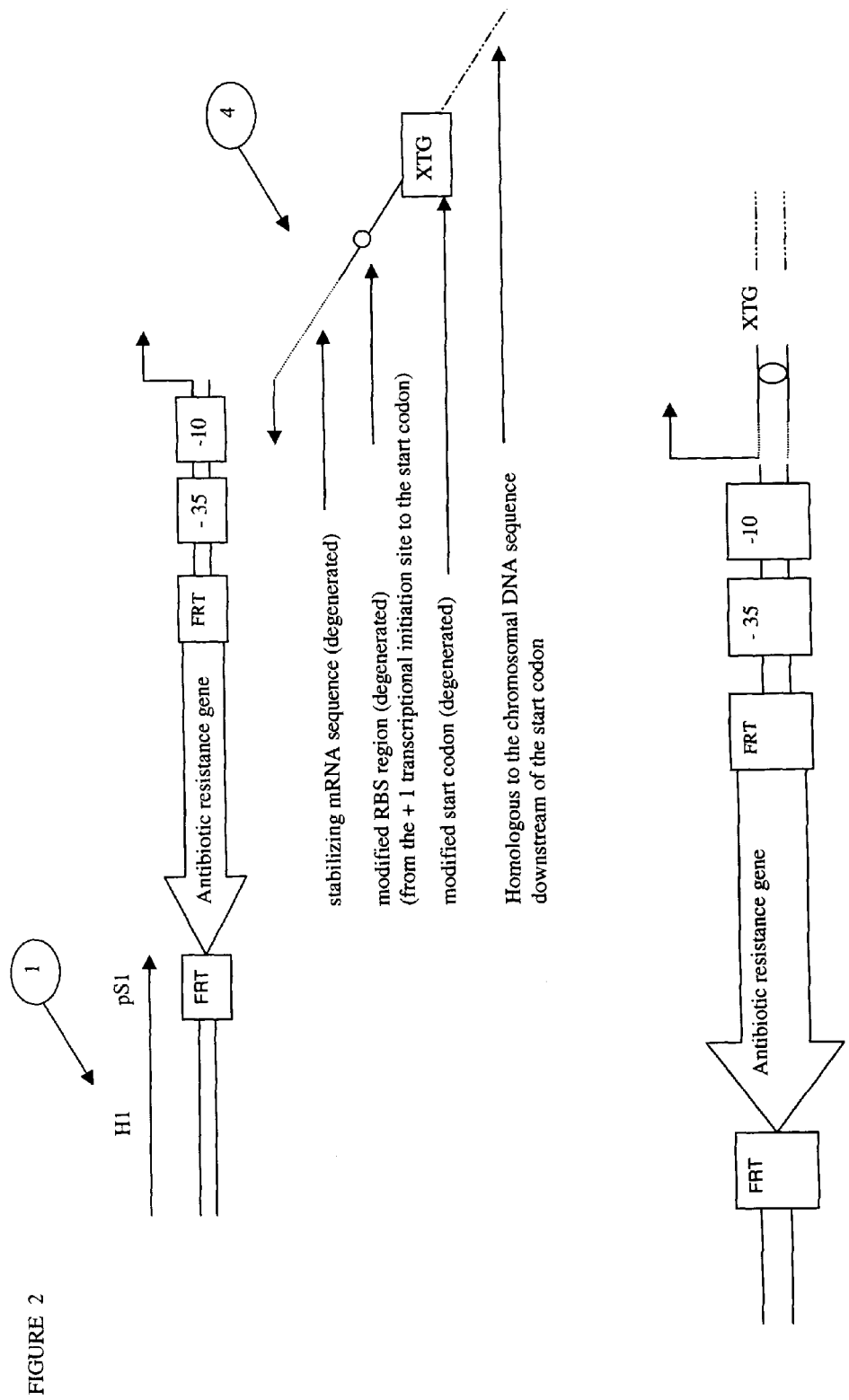
FIG. 2 is a schematic representation of the method of creating a DNA library comprising artificial promoters, modified ribosome binding sites, mRNA stabilizing sequences, and/or modified start codons according to the invention. In this figure, the mixture of double stranded PCR products of FIG. 1 are mixed in a further PCR reaction with the oligonucleotide (1) and a third oligonucleotide (4) comprising a nucleic acid fragment homologous to the 5' end of the gene of interest (which is the same gene of interest in FIG. 1) a start codon, which may be a modified start codon; a modified ribosome binding site of the precursor promoter; a stabilizing mRNA segment and a nucleic acid fragment homologous to a downstream region of the start codon of the gene of interest to obtain a new mixture of double stranded PCR products. X indicates that the start codon may be modified.
Figure 3:
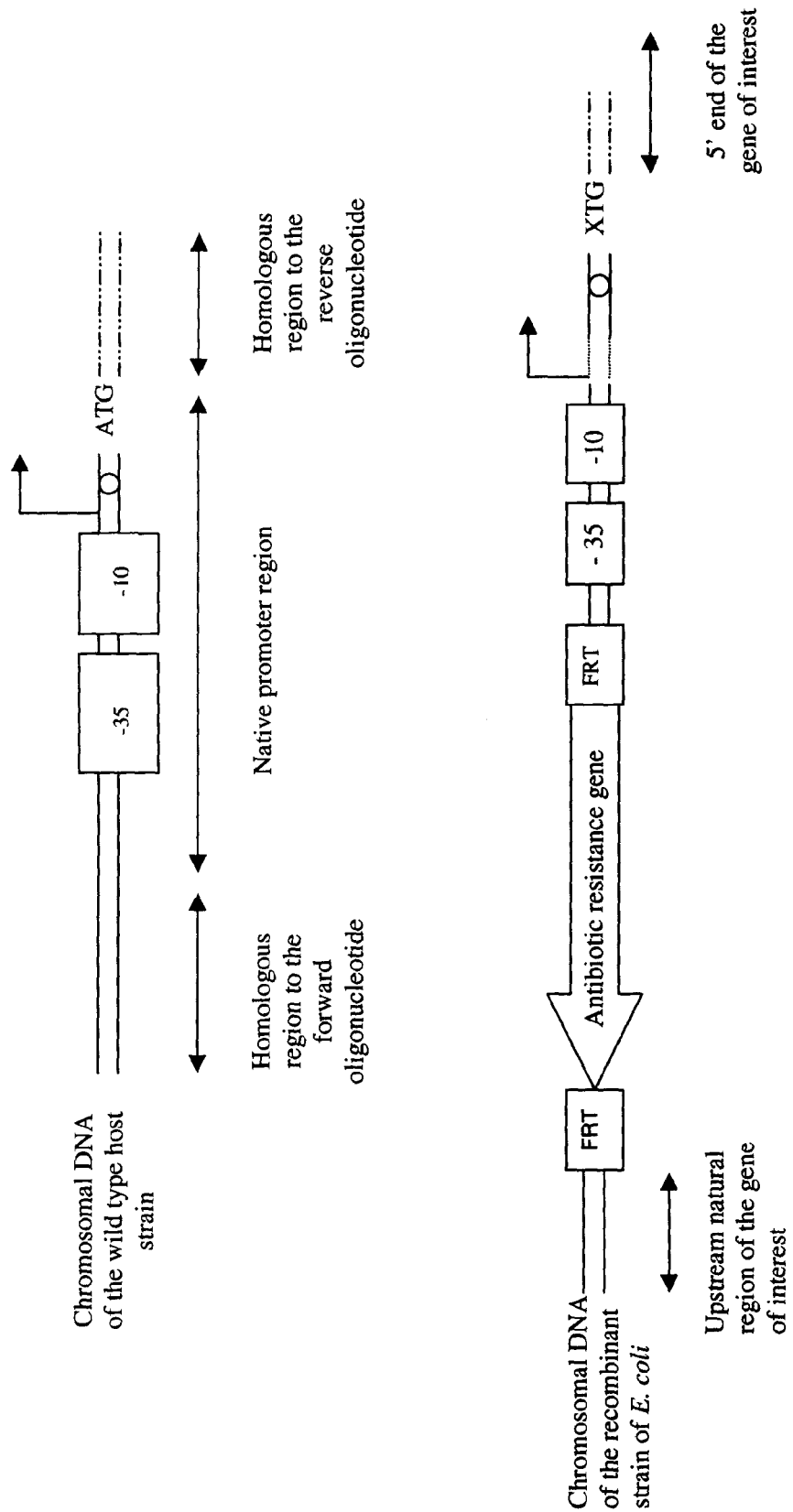
FIG. 3 is a schematic representation of the replacement of a chromosomal regulatory sequence with the PCR products according to the invention.
Figure 5:
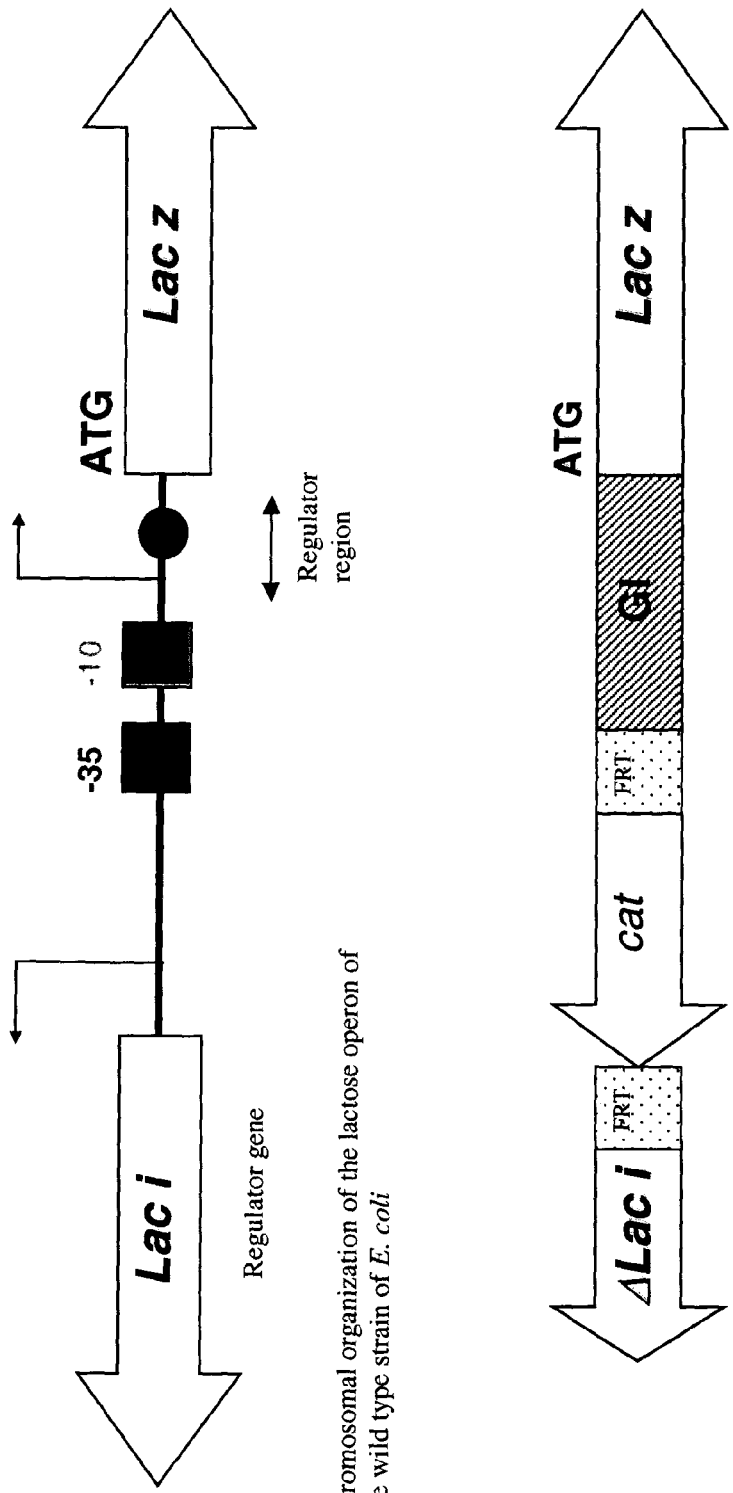
FIG. 5 compares the chromosomal organization of the lactose operon of the wild-type strain (A) and chromosomal organization of a host strain transformed with a promoter (B) according to the invention.

```
A = CAAGGAGGAA ACAGCTATG,    (SEQ ID NO. 22)
B = CAAGAAGGAA ACAGCTATG,    (SEQ ID NO. 23)
C = CACACAGGAA ACAGCTATG,    (SEQ ID NO. 24)
D = CTCACAGGAG ACAGCTATG,    (SEQ ID NO. 25)
E = CTCACAGGAA ACAGCTATG,    (SEQ ID NO. 26)
F = CACACAGAAA ACAGCTATG,    (SEQ ID NO. 27)
G = CTCACAGAGA ACAGCTATG,    (SEQ ID NO. 28)
and
H = CTCACAGAAA ACAGCTATG.    (SEQ ID NO. 29)
```

FIG. 9 illustrates the expression of the lacZ gene with the 1.6GI promoter (SEQ ID NO. 19), wherein the ribosome binding site (AGGAAA) has been altered and a stabilizing mRNA sequence has been inserted.

DETAILED DESCRIPTION OF THE INVENTION

The present invention relates to a method of creating a library of bacterial clones from amplified DNA libraries, particularly PCR generated DNA libraries, wherein the bacterial clones express a chromosomal gene of interest at different levels. The generated DNA libraries include any one of the following libraries, artificial promoters, ribosome binding sites (RBS), start codons and mRNA stabilizing sequences. An advantage of the method disclosed herein is that only one in vivo step is required to create the library of bacterial clones.

One aspect of the present invention relates to the discovery, that gene expression level is changed by altering one or two nucleotides in the −35 consensus region (−35 box), the −10 consensus region (−10 box), the linker region, the RBS, and/or the start codon and further that the alteration allows a quick identification of a range of gene expression that would produce a significant phenotypic change. A second aspect, the invention relates to the use of precursor promoter sequences, RBSs, start codons and/or mRNA stabilizing sequences which are contained within one or two degenerated oligonucleotides so that the DNA library may be generated by one or two amplification steps.

Definitions

Within this application, unless otherwise stated, illustration of the techniques used may be found in any of several well-known references such as: Sambrook, J., et al., MOLECU- LAR CLONING: A LABORATORY MANUAL, Cold Spring Harbor Laboratory Press (1989); Goeddel, D., ed., GENE EXPRESSION TECHNOLOGY, METHODS IN ENZYMOLOGY, 185, Academic Press, San Diego, Calif. (1991); "GUIDE TO PROTEIN PURIFICATION" in Deutshcer, M. P., ed., Methods in Enzymology, Academic Press, San Diego, Calif. (1989); and, Innis, et. al., PCR PROTOCOLS: A GUIDE TO METHODS AND APPLICATIONS, Academic Press, San Diego, Calif. (1990). Unless defined otherwise, all technical and scientific terms used herein have the same meaning as commonly understood by one or ordinary skill in the art to which this invention pertains. Both Singleton et al., DICTIONARY OF MICROBIOLOGY AND MOLECULAR BIOLOGY, 2D. Ed., John Wiley and Sons, New York (1994) and Hale and Martin, THE HARPER COLLINS DICTIONARY OF BIOLOGY, Harper Perennial, New York (1991) provide one of skill in the art with general dictionaries of many of the terms used in this invention.

Although any methods and materials similar or equivalent to those described herein can be used in the practice or testing of the present invention, the preferred methods and materials are described. Numeric ranges are inclusive of the numbers defining the range.

Unless otherwise indicated, nucleic acids are written left to right in 5' to 3' orientation; amino acid sequences are written left to right in amino to carboxy orientation, respectively. The headings provided herein are not limitations of the various aspects or embodiments of the invention which can be had by reference to the specification as a whole. Accordingly, the terms defined immediately below are more fully defined by reference to the specification as a whole. The references, issued patents and pending patent applications cited herein are incorporated by reference into this application.

For the purpose of this invention "a DNA library" includes any one or a combination of the following, artificial promoter libraries, modified ribosome binding site (RBS) libraries, modified start codon libraries, and stabilizing mRNA libraries. While a library may include $10^3$ or more members, in preferred embodiments a library will include at least 2, at least 3, at least 4, at least 6, at least 8, at least 16 or at least 64 members. A DNA library also referes to double stranded DNA molecules.

For the purposes of this application, a "promoter" or "promoter region" is a nucleic acid sequence that is recognized and bound by a DNA dependent RNA polymerase during initiation of transcription. The promoter, together with other transcriptional and translational regulatory nucleic acid sequences (also termed "control sequences") is necessary to express a given gene or group of genes (an operon). In general, the transcriptional and translational regulatory sequences include, but are not limited to, promoter sequences, ribosomal binding sites, transcriptional start and stop sequences, translational start and stop sequences, and enhancer or activator sequences. The "transcription start site" means the first nucleotide to be transcribed and is designated +1. Nucleotides downstream of the start site are numbered +2, +3, +4 etc., and nucleotides in the opposite (upstream) direction are numbered −1, −2, −3 etc. A promoter may be a regulatable promoter, such as Ptrc, which is induced by IPTG or a constitutive promoter.

In the context of the present invention, a promoter includes two consensus regions. A consensus region is a distinct group of conserved short sequences recognized by RNA polymerases differing in their sigma factors. One consensus region is centered about 10 base pairs (bp) upstream from the start site of transcription initiation and is referred to as the −10 consensus region (−10 box or Pribnow box). The other consensus region is centered about 35 bp upstream of the transcriptional start site and is referred to as the −35 consensus region (−35 box). A linker sequence extends between each consensus region and is comprised of about 14 to 20 bp.

A precursor promoter according to the invention may be a native (endogenous) promoter or an exogenous promoter. Further a precursor promoter may be a genetically engineered promoter that is either heterologous or homologous to a gene of interest. Generally precursor promoters will be in the range of 250 to 25 base pairs (bp); 150 to 25 bp; 100 to 25 bp; 75 to 25 bp and preferably 50 to 30 bp from the transcription start site (+1).

An "artificial promoter" according to the invention is a precursor promoter that has been modified by altering a nucleotide in at least one position corresponding to a position in the −35 box, the −10 box and/or the linker sequence. In a preferred embodiment, an artificial promoter will comprise 30 to 50 bp upstream of the transcription start site (+1) and will be derived from a precursor promoter having 50 to 30 bp.

A "library of promoters" refers to a population of promoters which includes artificial promoters, having at least two members. In one embodiment a library will be derived from the same precursor promoter.

A "ribosome binding site" (RBS) is a short nucleotide sequence usually comprising about 4-16 base pairs and functions by positioning the RBS on the mRNA molecule for translation of an encoded protein. A "modified ribosome binding" site is a ribosome binding site wherein one or more base pairs have been altered. A preferred modified RBS is derived from the same regulatory region as a precursor promoter when both the precursor promoter and RBS are modified and used in the same library. A library of modified ribosome binding sites includes at least two modified ribosome binding sites derived from the same precursor.

A "stabilizing mRNA" is a nucleic acid sequence insert used to influence gene expression. These inserts are generally located between the transcription and translational start sites of a gene or nucleic acid sequence.

A "library of bacterial clones" refers to a population of bacterial cells grown under essentially the same growth conditions and which are identical in most of their genome but include a DNA library as defined herein which may comprise for example a library of artificial promoters. A library of bacterial clones will have different levels of expression of the same gene of interest.

As used herein, the term "nucleic acid" includes RNA, DNA and cDNA molecules. It will be understood that, as a result of the degeneracy of the genetic code, a multitude of nucleotide sequences encoding a given protein may be produced. The term nucleic acid is used interchangeably with the term "polynucleotide". An "oligonucleotide" is a short chain nucleic acid molecule. A primer is an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "gene" means the segment of DNA involved in producing a polypeptide chain, that may or may not include regions preceding and following the coding region (e.g. 5' untranslated (5' UTR) or "leader" sequences and 3' UTR or "trailer" sequences), as well as intervening sequences (introns) between individual coding segments (exons).

As used herein the term "polypeptide" refers to a compound made up of amino acid residues linked by peptide bonds. The terms protein, peptide and polypeptide are used interchangeably herein.

The term "modification" includes a deletion, insertion, substitution or interruption of at least one nucleotide or amino acid in a sequence.

As used herein, a "deletion" is defined as a change in either a nucleotide or amino acid sequence in which one or more nucleotides or amino acid residues, respectively, are absent.

As used herein, an "insertion" or "addition" is that change in a nucleotide or amino acid sequence which has resulted in the addition of one or more nucleotides or amino acid residues, respectively, as compared to a parent sequence.

As used herein, a "substitution" results from the replacement of one or more nucleotides or amino acids by different nucleotides or amino acids, respectively.

In one embodiment a modified DNA sequence is generated with site saturation mutagenesis in at least one nucleotide. In another embodiment, site saturation mutagenesis is performed for two or more nucleotides. In a further embodiment, a modified or mutant DNA sequence has more than 40%, more than 45%, more than 50%, more than 55%, more than 60%, more than 65%, more than 70%, more than 75%, more than 80%, more than 85%, more than 90%, more than 95%, more than 96%, more than 97%, or more than 98% homology with a wild-type sequence from which it was modified from. In alternative embodiments, mutant DNA is generated in vivo using any known mutagenic procedure such as, for example, radiation, nitrosoguanidine and the like.

A nucleic acid is "operably linked" when it is placed into a functional relationship with another nucleic acid sequence. For example, a promoter is operably linked to a coding sequence if it affects the transcription of the sequence; or a ribosome binding site is operably linked to a coding sequence if it is positioned so as to facilitate translation. Linking of nucleic acid sequences may be accomplished by ligation at convenient restriction sites. If such sites do not exist, synthetic oligonucleotide adaptors or linkers may be used in accordance with conventional practice.

As used herein a "DNA construct" refers to a nucleic acid sequence or fragment that is used to introduce sequences into a host cell or organism. The DNA may be generated in vitro by PCR or any other suitable techniques. In some embodiments a DNA construct according to the invention comprises homologous upstream (5') and/or homologous downstream (3') sequences to a precursor promoter, a gene of interest or to another DNA segment. In yet another embodiment a DNA construct may be inserted into a vector. The DNA constructs may include homologous or heterologous sequences to a host cell gene and further may include a combination of heterologous sequences and homologous sequences. In some embodiments, a DNA construct will include a selective marker gene. In other embodiments, a DNA construct will include an artificial promoter and in other embodiments a DNA construct will include a modified RBS sequence, a modified translational start codon and stabilizing mRNA sequences. These DNA constructs are sometimes referred to herein collectively or individually as "regulatory DNA constructs".

As used herein, the term "vector" refers to a nucleic acid construct designed for transfer between different host cells. A vector may be a plasmid, a bacteriophage, a cloning vector, a shuttle vector or an expression vector. An "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those having skill in the art. Vectors used in the process of the may be any vector suitable for isolation and characterization of a promoter.

As used herein, a "flanking sequence" refers to any sequence that is either upstream or downstream of the sequence being discussed (e.g., for genes A B C, gene B is flanked by the A and C gene sequences). In some embodiments, a flanking sequence is present on only a single side (either 3' or 5') of a DNA fragment, but in preferred embodiments, it is on each side of the sequence being flanked.

As used herein the terms, "heterologous nucleic acid sequence" or heterologous DNA construct" refers to a portion of a genetic sequence that is not native to the cell in which it is expressed. "Heterologous," with respect to a control sequence refers to a control sequence (i.e., promoter) that does not function in nature to regulate the same gene the expression of which it is currently regulating. Generally, heterologous nucleic acid sequences are not endogenous to the cell or part of the genome in which they are present, and have been added to the cell, by infection, transfection, microinjection, electroporation, or the like. In some embodiments, "heterologous nucleic acid constructs" contain a control sequence/DNA coding sequence combination that is the same as, or different from a control sequence/DNA coding sequence combination found in the native cell.

As used herein, "homology" refers to sequence similarity or identity, with identity being preferred. This homology is determined using standard techniques known in the art (See e.g., Smith and Waterman, *Adv. Appl. Math.*, 2:482 (1981); Needleman and Wunsch, *J. Mol. Biol.*, 48:443 (1970); Pearson and Lipman, *Proc. Natl. Acad. Sci.* USA 85:2444 (1988); programs such as GAP, BESTFIT, FASTA, and TFASTA in the Wisconsin Genetics Software Package (Genetics Computer Group, Madison, Wis.); and Devereux et al., *Nucl. Acid Res.*, 12:387-395 (1984)).

The term "target site" is intended to mean a predetermined genomic location within a bacterial chromosome where integration of a DNA construct or a DNA library is to occur.

As used herein, the term "chromosomal integration" refers to the process whereby an exogenous nucleic acid sequence is introduced into the chromosome of a host cell (e.g., *Bacillus*). The homologous sequences of the exogenous nucleic acid sequence align with homologous regions of the chromosome. Subsequently, the sequence between the homologous regions of the chromosomal sequence is replaced by the incoming exogenous sequence in a double crossover (i.e., homologous recombination).

As used herein, the term "introduced" used in the context of inserting a nucleic acid sequence into a cell, means "transfection," "transformation," or "transduction," and includes reference to the incorporation of a nucleic acid sequence into a eukaryotic or prokaryotic cell where the nucleic acid sequence may be incorporated into the genome of the cell (e.g., chromosome, plasmid, plastid, or mitochondrial DNA), converted into an autonomous replicon, or transiently expressed (for example, transfected mRNA).

As used herein, the terms "transformed," "stably transformed," and "transgenic" used in reference to a cell means the cell has a non-native (heterologous) nucleic acid sequence integrated into its genome or as an episomal plasmid that is maintained through two or more generations.

As used herein " an insertion DNA construct" or "insertion DNA cassette" is a DNA construct that includes a selectable marker gene which is flanked on both sides by a recombinase recognition site. A "recombinase recognition site" is a novel recombination site that facilitates directional insertion of nucleotide sequences into corresponding recombination sites at a predetermined genomic location (a target site) within the bacterial chromosome where the integration of a DNA fragment is to occur.

As used herein, the term "selectable marker" refers to a gene capable of expression in host cell which allows for ease of selection of those hosts containing an introduced nucleic acid or vector. Examples of such selectable markers include but are not limited to antimicrobials, (e.g., kanamycin, erythromycin, actinomycin, chloramphenicol and tetracycline). Thus, the term "selectable marker" refers to genes that provide an indication that a host cell has taken up an exogenous polynucleotide sequence or some other reaction has occurred. Typically, selectable markers are genes that confer antimicrobial resistance or a metabolic advantage on the host cell to allow cells containing the exogenous DNA to be distinguished from cells that have not received any exogenous sequence during the transformation.

As used herein, the terms "amplification" and "gene amplification" refer to a process by which specific DNA sequences are disproportionately replicated such that the amplified nucleic acid sequence becomes present in a higher copy number than was initially present in the genome. The term also refers to the introduction into a single cell of an amplifiable marker in conjunction with other gene sequences (i.e., comprising one or more non-selectable genes such as those contained within an expression vector) and the application of appropriate selective pressure such that the cell amplifies both the amplifiable marker and the other, non-selectable gene sequences. The amplifiable marker may be physically linked to the other gene sequences or alternatively two separate pieces of DNA, one containing the amplifiable marker and the other containing the non-selectable marker, may be introduced into the same cell.

As used herein, the term "polymerase chain reaction" ("PCR") refers to the methods of U.S. Pat. Nos. 4,683,195; 4,683,202, and 4,965,188, hereby incorporated by reference, which include methods for increasing the concentration of a segment of a polynucleotide or target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. Because the desired amplified segments of the target sequence become the predominant sequences (in terms of concentration) in the mixture, they are said to be "PCR amplified".

As used herein, the term "PCR product," refers to the resultant mixture of compounds after two or more cycles of the PCR steps of denaturation, annealing and extension are complete. These terms encompass the case where there has been amplification of one or more segments of one or more target sequences. The term double stranded amplified products includes PCR products.

As used herein, the term "restriction enzymes" refers to bacterial enzymes, each of which cut double-stranded DNA at or near a specific nucleotide sequence.

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process itself are, themselves, efficient templates for subsequent PCR amplifications.

As used herein, "host cell" refers to a cell that has the capacity to act as a host and expression vehicle for an introduced DNA (exogenous) sequence according to the invention.

As used herein the term "expression" refers to the process by which a polypeptide is produced based on the nucleic acid sequence of a gene. The process includes both transcription and translation.

A "range of expression levels" means the expression of a gene of interest obtained from a library of bacterial clones transformed with PCR generated DNA libraries. In one embodiment, the level of expression in a clone library will range from 1 to 500%, compared to the expression of a control which includes a precursor or native promoter and regulatory region when grown under essentially the same conditions.

"Optimal expression" refers to the cumulative conditions that provide an optimal level of gene expression for a particular coding region. Under certain laboratory conditions, optimal expression means a lower level of gene expression and under other conditions, optimal expression means a higher level of gene expression that can coexist in a cell in situations where, under certain conditions the expressed gene or product produced therefrom would be detrimental to the viability of the cells or have an adverse effect upon the cells.

"Isolated" as used herein refers to a nucleic acid or polypeptide that is removed from at least one component with which it is naturally associated.

The term "comprises and its cognates are used in their inclusive sense: that is equivalent to the term including and its cognates.

"A", "an" and "the" include plural references unless the context clearly dictates otherwise.

Preferred Embodiments of the Invention

Promoter sequences useful for creating artificial promoters according to the invention include the precursor promoters listed in Table 1 below. FIG. 4 illustrates the sequence of some of these precursor promoters including the −35 box, −10 box and linker region. All promoters in the table are characterized with respect to the beta-lactamase promoter Pbla and promoter strengths are given in "Pbla-units". (Deuschle et al., *EMBO Journal* 5(11):2987-2994 (1986)).

In general, promoters useful in the invention include promoter sequences of between 200 to 20 base pairs (bp), preferably 150 to 25 bp, more preferably between 100 to 30 bp and most preferably between 50 to 30 bp upstream from the transcription start site (+1). The shorter sequences (between 50 to 30 bp) are most preferred because DNA libraries may be created more easily within a single degenerated oligonucleotide with the shorter sequences. Therefore in a preferred embodiment, a short sequence of the promoters as disclosed in FIG. 4 would be used to obtain artificial promoters according to the invention. These preferred sequences would include about 50 to 30 bp staring at about the transcriptional start site (+1) of said promoters.

TABLE 1

| PROMOTER | Source | Relative Activity | SEQ ID NO. |
| --- | --- | --- | --- |
| β-lactamase (bla) | *E. coli* vector | 1 | 14 |
| PConsensus (con) | Synthetic DNA | 4 | 13 |
| PTac I (Trc) | Hybrid of 2 promoters | 17 | 2 |
| PLacUV5 | Mutant of Lac | 3.3 | 12 |
| Plac | *E. coli* lacZ gene | 5.7 | 1 |
| PL | Phage λ | 37 | 11 |
| PA1 | Phage T7 | 22 | 8 |
| PA2 | Phage T7 | 20 | 9 |
| PA3 | Phage T7 | 76 | 10 |
| PJ5 | Phage T5 | 9 | 7 |
| PG25 | Phage T5 | 19 | 6 |
| PN25 | Phage T5 | 30 | 5 |
| PD/E20 | Phage T5 | 56 | 4 |
| PH207 | Phage T5 | 55 | 3 |

Additional promoters useful in the invention are disclosed in Sommer et al., (2000) *Microbiol.* 146:2643-2653, wherein the sequence of Ptac and variants containing 1 or 2 base pair changes are taught. In one embodiment a preferred precursor promoter is a trc promoter (Ptrc). The −35 box (TTGACA) and the −10 box (TATAAT) is the same as Ptac. However, the linker region of Ptrc includes 17 bp as compared to 16 bp for Ptac. There is an addition of a "C" between nucleotides −18 and −10 of Ptac. (Russell and Bennett, (1982) *Gene:* 20:231 and Amann et al., (1983) *Gene* 25:167-178).

A further useful promoter is the glucose isomerase promoter $P_{GI}$. This promoter is also known in the literature as a xylose isomerase promoter and reference is made to Amone et al., (1989) *Appl. Microbiol. Biotechnol.* 30:351-357. The $P_{GI}$ comprises the following GCCC<u>TTGACA</u> ATGCCACATCCTGAGCA <u>AATAAT</u> TCAACCACT<u>A</u> ATTGTGAGCGGATAACA (SEQ ID NO. 15), wherein the −35 box is represented by TTGACA, the −10 box is represented by AATAAT and the +1 transcription start site is <u>A</u>.

In addition to the above promoters, a variety of precursor promoters can be utilized in the practice of the present invention. In some cases, strong promoters tend to be overexpressed to the detriment of the host cell viability. Cells use a limited set of signals to engage the transcriptional machinery and transcribe a gene. Bacteria such as *E.coli*, uses a core RNA polymerase and several sigma subunits to recognize different type of promoters (deHaseth et al. 1998. *J. Bact.* 180: 3019-3025. The *E. coli* genes required for fast growth are mainly under the control of the sigma factor coded by the rpoD gene. The most obvious components of a RpoD-dependent promoter are the −35 and −10 regions that contain variations of the consensus sequences TTGACA and TATAAT respectively. The promoter region contains 2 other components that affect promoter strength in a subtler manner: the upstream (Gourse et al., 2000. *Mol. Microbiol.* 37: 687-695) and the spacer regions (Burr et al. (2000) *NAR* 28: 1864-1870). The contribution of each one of these 2 elements varies depending on how similar the −35 and −10 region are to the consensus.

A precursor promoter used to obtain a library of artificial promoters as described herein may be determined by various exemplary methods. While not wanting to be limited, in one embodiment, sequencing of a particular host genome may be performed and putative promoter sequences identified using computerized searching algorithms. For example, a region of a genome may be sequenced and analyzed for the presence of putative promoters using Neural Network for Promoter Prediction software, NNPP. NNPP is a time-delay neural network consisting mostly of two feature layers, one for recognizing TATA-boxes and one for recognizing so called "initiators", which are regions spanning the transcription start site. Both feature layers are combined into one output unit. Further identification of precursor promoter sequences can be identified by examination of putative promoter sequences identified in a genome of a host cell using homology analysis. For example, by using BLAST. These putative sequences may then be cloned into a cassette suitable for preliminary characterization in *E. coli* and/or direct characterization in *E. coli*.

In another embodiment, identification of consensus promoter sequences can be identified by examination of the family of genomes and putative promoter sequences identified in the genome in question using homology analysis. For example, a homology study of a family of genomes may be performed and analyzed for the presence of putative consensus promoters using BLAST. These putative promoter sequences may then be cloned into a cassette suitable for preliminary characterization in *E. coli*.

An artificial promoter according to the invention will comprise at least one modification to a nucleotide in a precursor promoter. In one embodiment the modification will be to a nucleotide positioned in the −35 consensus region. This modification may include a modification to one or more nucleotides at a position equivalent to a nucleotide at the −30, −31, −33, −34, −35, and/or −36 position of a precursor promoter. Preferably the modification will be of one or two nucleotides, and preferably the modification will be a substitution of one nucleotide or two nucleotides. When two positions are to be modified, four positions will be conserved, and when one position is modified, five positions will be conserved. In another embodiment the modification will include a modification to the nucleotide represented by position −30 and/or a change to a position corresponding to −35.

In preferred embodiments, an artificial promoter is obtained from a precursor promoter having a −35 box represented by the following sequences, TTGACA, TTGCTA, TTGCTT, TTGATA, TTGACT, TTTACA and TTCAAA. Particularly preferred −35 consensus regions from precursor promoters are TTTACA and TTGACA. As a non-limiting example when TTGACA is the −35 box of a precursor promoter, the nucleotide at position −30 is A and it may be substituted with a T, G or C nucleotide, the nucleotide at position −31 is C and it may be substituted with a A, T or G nucleotide; the nucleotide at position −32 is A and it may be substituted with a T, G or C nucleotide; the nucleotide at position −33 is G and it may be substituted with a A, T, or C nucleotide; the nucleotide at position −34 is T and it may be substituted with a A, G or C nucleotide; and the nucleotide at position −35 is T and it may be substituted with a A, G or C nucleotide.

In another embodiment, the modification will be in the −10 consensus region. This modification may include a modification to one or more nucleotides at a position corresponding to the −7, −8, −9, −10, −11, and/or −12 position of a precursor promoter. Preferably the modification will be in one or two nucleotide positions. In a particularly preferred embodiment, the precursor promoter will include the following sequences of the −10 box, TAAGAT, TATAAT, TATACT, GATACT, TACGAT, AATAAT, TATGTT and GACAAT. Particularly preferred are the sequences TATAAT, TATGTT, AATAAT and TAAGAT and most preferred are TATAAT and AATAAT. In one particular embodiment, the precursor promoter is the trc promoter and most particularly the 50 to 30 bp sequence upstream of the +1 transcription start site and the artificial promoter will include at least one modification to a nucleotide in the −10 box represented by TAAGAT. For example, since the nucleotide at position −7 is T, it may be substituted with a C, G or A nucleotide; since the nucleotide at position −8 is A, it may be substituted with a C, G or T nucleotide; since the nucleotide at position −9 is G, it may be substituted with a C, T or A; since the nucleotide at position −10 is A, it may be substituted with a T, C or G nucleotide; since the nucleotide at position −11 is A, it may be substituted with a T, C or G nucleotide; and since the nucleotide at position −12 is T, it may be substituted with a C, G or T nucleotide.

In some embodiments of the invention, both the −35 box and the −10 box of the precursor promoter will have modifications. In one embodiment, the modification will include one nucleotide in each consensus region, and in a further embodiment the modification will include two nucleotides in each consensus region. In another embodiment a modification will include a modification to the −35 box represented by TTGACA and a modification to the −10 box represented by AATAAT. In another embodiment the modification will include a modification to the −35 box represented by TTGACA and a modification to the −10 box represented by TATAAT.

The linker sequence of a precursor promoter may also be modified to obtain an artificial promoter according to the invention. The precursor linker sequence may include deletions, substitutions or insertions. Preferably the linker sequence is between 14 and 20 base pairs in length. The length of the linker sequence may be modified to optimize expression by performing deletion analysis, such as by site directed mutagenesis to create sequential deletions in the precursor promoter. The linker sequence or the precursor promoter may be modified in length to include 16 base pairs, 17 base pairs, 18 base pairs, 19 base pairs or 20 base pairs.

In one embodiment, modified DNA sequences in the precursor promoter are generated by using a degenerated oligonucleotide in accordance with well know techniques. In a preferred embodiment, the artificial promoters will comprise 30 to 50 bp upstream of the transcription site (+1) so that the promoter could be contained within an oligonucleotide and the library of promoters created by degeneration of the oligonucleotide.

Promoter strength can be quantified using in vitro methods that measure the kinetics of binding of the RNA polymerase to a particular piece of DNA, and also allows the measurement of transcription initiation (Hawley D. K et al., Chapter 3: in: PROMOTERS: STRUCTURE AND FUNCTION. R. L/Rodriguez and M. J. Chamberlin eds. Praeger Scientific. New York). In vivo methods have been used also to quantify promoter strength. In this case, the approach has been to fuse the promoter to a reporter gene and the efficiency of RNA synthesis measured.

To create DNA libraries which comprise a library of artificial promoters, a first degenerated oligonucleotide comprising a nucleic acid sequence homologous to a first end, preferably the 3' end, of an insertion DNA construct, a promoter as described above, and a nucleic acid sequence homologous to the downstream region of the transcription start site of a precursor or native promoter is mixed with both i) a second oligonucleotide which comprises a nucleic acid sequence homologous to an upstream region of the precursor or native promoter of a chromosomal gene of interest and a nucleic acid sequence homologous to a second end, preferably the 5' end, of the insertion DNA construct, and ii) an insertion DNA construct in an amplification reaction, preferably a PCR reaction to obtain double stranded amplified products comprising artificial promoters.

In a preferred embodiment, an insertion DNA construct is carried on a plasmid, preferably on a R6K plasmid and comprises an antibiotic resistance gene flanked on both sides by a recombinase recognition site. (Datsenko and Warner (2000) *Proc. Natl. Acad. Sc.* 97:6640-6645). While any desired selective marker can be used, antibiotic resistant markers ($Anb^R$) are most useful. These include but are not limited to, $Cm^R$, $Km^R$ and $Gm^R$. Preferably, the recombinase recognition sites are the same. Recombinase sites are well-known in the art and generally fall into two distinct families based on their mechanism of catalysis and reference is made to Huang et al., (1991) *Nucleic Acids Res.* 19:443 and Nunes-Duby et al., (1998) *Nucleic Acid Res.* 26:391-406.

A preferred recombination system is the *Saccharomyces* Flp/FRT recombination system, which comprises a Flp enzyme and two asymmetric 34 bp FRT minimum recombination sites (Zhu et al., (1995) *J. Biol. Chem.* 270:11646-11653). A FRT sites comprises two 13 bp sequences, inverted and imperfectly repeated, which surround an 8 bp core asymmetric sequence where crossing-over occurs. The FLP-dependent intramolecular recombination between two parallel FRT sites results in excision of any intervening DNA sequence as a circular molecule producing two recombination products, each containing one FRT site (Huffman et al. (1999) *J. Mol. Biol.* 286: 1-13).

In general, nucleic acid sequences homologous to downstream regions or upstream regions may include from 2-150 bp, preferably 5-100 bp, more preferably 5-50 bp and also 10-40 bp. In specific embodiments a nucleic sequence homologous to the downstream transcription start site of the precursor or native promoter or a nucleic acid sequence homologous to an upstream region of the precursor promoter of a chromosomal gene of interest may include about 5 to 100 base pairs and also 5 to 50 base pairs. The nucleic acid homologous to a 5' or 3' end of the insertion DNA construct may include about 10 to 40 base pairs and preferably about 2 to 25 base pairs. An upstream region of the precursor promoter means a segment upstream (5') of the −35 consensus sequence.

In further embodiments of the invention a RBS, downstream of the precursor promoter region, may be modified. Preferred RBSs, which may be modified include the sequences selected from the following: AGGAAA, (SEQ ID NO. 30), AGAAAA (SEQ ID NO. 31), AGAAGA (SEQ ID NO. 32), AGGAGA (SEQ ID NO. 33), AAGAAGGAAA (SEQ ID NO. 34), AAGGAAAA (SEQ ID NO. 35), AAGGAAAG (SEQ ID NO. 36), AAGGAAAU (SEQ ID NO. 37), AAGGAAAAA (SEQ ID NO. 38), AAGGAAAAG (SEQ ID NO. 39), AAGGAAAAU (SEQ ID NO. 40), AAGGAAAAAA (SEQ ID NO. 41), AAGGAAAAAG (SEQ ID NO. 42), AAGGAAAAAU (SEQ ID NO. 43), AAGGAAAAAAA (SEQ ID NO. 44), AAGGAAAAAAG (SEQ ID NO. 45), AAGGAAAAAAU (SEQ ID NO. 46), AAGGAAAAAAAA (SEQ ID NO. 47), AAGGAAAAAAAG (SEQ ID NO. 48), AAGGAAAAAAAU (SEQ ID NO. 49), AAGGAAAAAAAAA (SEQ ID NO. 50), AAGGAAAAAAAAG (SEQ ID NO. 51), AAGGAAAAAAAAU (SEQ ID NO. 52), AAGGAAAAAAAAAA (SEQ ID NO. 53), AAGGAAAAAAAAAG (SEQ ID NO. 54), AAGGAGGAAA (SEQ ID NO. 55), and AAGGAAAAAAAAAU (SEQ ID NO. 56). Most preferred RBS include AGGAAA, (SEQ ID NO. 30), AGAAAA (SEQ ID NO. 31), AGAAGA (SEQ ID NO. 32), AGGAGA (SEQ ID NO. 33), and AAGGAGGAAA (SEQ ID NO. 55). The modified RBS may include substitution, deletion or insertion of anyone of the base pairs comprising the RBS.

To obtain DNA libraries comprising modified RBS libraries, a oligonucleotide comprising a nucleic acid fragment homologous to a downstream region of the −10 box of a promoter or artificial promoter, a modified RBS, and a nucleic acid fragment homologous to the 5' end of the chromosomal gene of interest which includes the start codon, is mixed with the double stranded amplified products comprising artificial promoters as described above and under similar PCR reactions. The homologous nucleic acid fragments may comprise from 2 to 100 base pairs and preferably from 2 to 50 base pairs. In other embodiments the (XTG) start codon of the gene of interest may be modified. These modifications may include X=A, T, G, depending on the native start codon in the gene of interest.

In other embodiments of the method described herein a stabilizing mRNA sequence may be incorporated into an oligonucleotide. The oligonucleotide may comprise an artificial promoter, a modified ribosome binding or both. The stabilizing sequences are preferably inserted between the RBS and the transcription start site.

Stabilizing mRNA sequence are well known in the art and reference is made to Carrier et al. (1999) *Biotechnol. Prog.* 15:58-64. Preferred mRNA stabilizing sequences include the sequences
GGTCGAGTTATCTCGAGTGAGATATTGTTGACG, (SEQ ID NO. 63);
GGTGGACTTATCTCGAGTGAGATATTGTTGACG, (SEQ ID NO. 64);
CCTCGAGTTATCTCGAGTGAGATATTGTTGACG, (SEQ ID NO. 65);
GCTCGAGTTATCTCGAGTGAGATATTGTTGACG, (SEQ ID NO. 66);
CGTCGAGTTATCTCGAGTGAGATATTGTTGACG, (SEQ ID NO. 67);
GGTGGAGTTATCTCGAGTGAGATATTGTTGACG, (SEQ ID NO. 68) and
GCTGGACTTATCTCGAGTGAGATATTGTTGACG, (SEQ ID NO. 69). In a preferred embodiment the stabilizing sequence is SEQ ID NO. 67. The double stranded amplified products may also include modified start codons of a gene of interest.

The double stranded amplified products which comprise artificial promoters, modified ribosome binding sites, modified start codons, stabilizing mRNA sequences and combinations thereof, according to the invention may be used individually and introduced into a host cell. Additionally, the double stranded amplified products may be used in a DNA library wherein said library comprises one or more of a library of artificial promoters, a library of modified ribosome binding sites, a library of modified start codons and which may or may not include stabilizing mRNA sequences. The DNA libraries are introduced into bacterial host cells wherein they replace the chromosomal regulatory regions of a gene of interest. Preferably the double stranded amplified products are integrated into the host cell chromosome. Flanking homologous regions of the double stranded amplified products replace homologous regions at a target site in a gene sequence of interest in a host chromosome. In a preferred embodiment, the integration of the PCR products is a stable and non-reverting integration. Preferably replacement is by a double crossover (i.e., homologous recombination). The introduced PCR products may create a library of bacterial cells having a range of expression levels for a gene of interest.

The method as disclosed herein is not limited to expression of any particular gene or group of genes (an operon), but is intended to be broadly applicable to many different genes or operons. In one preferred embodiment, the artificial promoters or other regulatory DNA constructs according to the invention will be operably linked to a coding sequence that was heterologous to a precursor promoter, and in another embodiment the artificial promoters or other regulatory DNA constructs will be operably linked to a coding sequence that was homologous to the precursor promoter. Further the coding sequence may be heterologous or endogenous to the host cell transformed according to the invention.

In some embodiments, the gene encodes therapeutically significant proteins or peptides, such as growth factors, hormones, cytokines, ligands, receptors and inhibitors, as well as vaccines and antibodies. A gene may also encode commercially important proteins or peptides, such as enzymes (e.g., proteases, amylases, glucoamylases, dehydrogenases, esterases, cellulases, galactosidases, oxidases, reductases, kinases, xylanases, laccases, phenol oxidases, chitinases, glucose oxidases, catalases, phytases, isomerases, phosphatases, and lipases). In further embodiments the gene of interest encodes global regulators; transporter proteins, such as glucose and/or DKG permeases, and enzymes from primary and secondary metabolism, such as tpi and nuo which code for triose phosphate isomerase and NADH dehydrogenase, respectively.

In one embodiment, the host cell is a bacterial cell such as a gram positive bacteria. In another embodiment the host cell is a gram-negative bacteria. In some preferred embodiments, the term refers to cells in the genus *Pantoea*, the genus *Bacillus* and *E. coli* cells.

As used herein, "the genus *Bacillus*" includes all members known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*." The production of resistant endospores in the presence of oxygen is considered the defining feature of the genus *Bacillus*, although this characteristic also applies to the recently named *Alicyclobacillus, Amphibacillus, Aneurinibacillus, Anoxybacillus, Brevibacillus, Filobacillus, Gracilibacillus, Halobacillus, Paenibacillus, Salibacillus, Thermobacillus, Ureibacillus*, and *Virgibacillus*.

As used herein, "the genus *Pantoea*" includes all members known to those of skill in the art, including but not limited to *P. agglomerans, P. dispersa, P. punctata, P. citrea, P. terrea, P. ananas* and *P. sterartii*. It is recognized that the genus *Pantoea* continues to undergo taxonomical reorganization. Thus, it is intended that the genus include species that have been reclassified, including but not limited to such organisms as *Erwinia herbicola*.

One skilled in the art are well aware of methods for introducing polynucleotides into host cells and particularly into *E. coli, Bacillus* and *Pantoea* host cells. General transformation techniques are disclosed in CURRENT PROTOCOLS IN MOLECULAR BIOLOGY Vol. 1, eds. Ausubel et al. John Wiley & Sons Inc, (1987) Chap. 7. and Sambrook, J., et al., MOLECULAR CLONING: A LABORATORY MANUAL, Cold Spring Harbor Laboratory Press (1989). Reference is also made to Ferrari et al., Genetics pgs 57-72 in Hardwood et al. Ed. BACILLUS, Plenum Publishing Corp. 1989; Chang et al., (1979) *Mol. Gen. Genet.* 168:11-15; Smith et al., (1986) *Appl. and Env. Microbiol.* 51:634 and Potter, H. (1988) *Anal Biochem* 174:361-373 wherein methods of transformation, including electroporation, protoplast transformation and congression; transduction and protoplast fusion are disclosed. Methods of transformations are particularly preferred.

Methods suitable for the maintenance and growth of bacterial cells is well known and reference is made to the Manual of Methods of General Bacteriology, Eds. P. Gerhardt et al., American Society for Microbiology, Washington, DC (1981) and T. D. Brock in Biotechnology: A Textbook of Industrial Microbiology 2 ed. (1989) Sinauer Associates, Sunderland Mass.

The transformed host cells are selected based on the phenotype response to a selectable marker which was provided in an insertion DNA construct. In some embodiments the selectable marker may be excised out of the host cell. (Cherepanov et al. (1995) *Gene* 158:9-14).

Additionally transformants may be analyzed to verify the integration of the regulatory DNA constructs, such as artificial promoters using various techniques. The regulatory DNA constructs including artificial promoters may be PCR verified using oligonucleotides outside the recombinase region. In one example the size of the PCR product obtained from the artificial promoter is compared to the size of the PCR product obtained from the reference promoter on an agarose gel. The regulatory DNA constructs may be verified by digesting the PCR product obtained from the artificial promoter with a restriction enzyme that is unable to digest the artificial promoter and that is able to digest the reference promoter. The regulatory DNA constructs may also be verified by evaluating gene expression and production. Many assays are known for measuring enzyme activity. For example beta-galactosidase is the enzyme produced by the lacZ gene, and the activity of this enzyme may be determine by the assay disclosed in Miller, J. H., A SHORT COURSE IN BACTERIAL GENETICS. Cold Spring Harbor Laboratory Press, 1992.

Additionally, the artificial promoter region and other regulatory regions in a host cell may be sequenced by means well known in the art. (Maxam et al., (1977) *PNAS* USA 74:560-564)

Transformed host cells according to the invention may have expression levels of a gene of interest which may be higher or lower that the expression level of the coding region of the gene in a parent control. In one embodiment the level of gene expression in a transformed host will be between about 1 to 500%, between about 1 to 250%, between about 5 to 200%, between about 10 to 150% and between about 10 to 100% of the level of expression of the same gene in the corresponding parent. Also about 5%, 15%, 25%, 35%, 45%, 55%, 65%, 70%, 75%, 80%, 85%, 90%, 95%, 100%, 120%, 140%, 160%, 180% and 200% the expression level of a corresponding parent.

Using a DNA library according to the invention, which includes an artificial promoter library, a modified RBS library, a mRNA stabilizing sequence library, or a start codon library or combinations thereof to create a population of bacterial cells having varying levels of expression of a gene of interest, is particularly useful in a metabolic engineering pathway framework.

A metabolic pathway is a series of chemical reactions that either break down a large molecule into smaller molecules (catabolism) or synthesize more complex molecules from smaller molecules (anabolism). Most of these chemical reactions are catalyzed by a number of enzymes. In many metabolic pathways there are rate-limiting enzymatic steps which serve to regulate the pathway. For example, in the glycolytic pathway wherein glucose is converted to pyruvate and ATP, phosphofructokinase is considered a key enzyme in regulation and in the pentose phosphate pathway wherein NADPH and ribose-5-phosphate are generated, glucose-6-phosphate dehydrogenase and fructose 1,6-diphosphatase are considered key enzymes.

In order to be commercially viable a chemical or protein must be capable of being produced and recovered in large quantities in an organism with low cultivation cost. Many industrial bioprocesses utilize whole-cell fermentation techniques. In many instances, the use of an isolated enzyme system is too expensive or impractical. Many enzymes, such as dehydrogenases that may be utilized to carry out chiral synthesis of pharmaceutical intermediates, require co-factors such as NAD(P) for their reactions. Cofactors are utilized stoichiometrically during the reaction and must be repeatedly added to the reaction mixture or the reaction must regenerate the cofactor. A whole-cell system provides an alternative for many of these enzymes. Other enzymes may be membrane-bound or require complex subunit or multi-enzyme complexes (such as cytochrome P-450s), allowing for simpler implementation using a whole-cell system. Finally, the synthesis of complex molecules such as steroids, antibiotics, and other pharmaceuticals may require complicated and multiple catalytic pathways.

In an isolated system, each step in a particular metabolic pathway would need to be engineered. In contrast, the organism utilized in a whole cell system provides each of the required pathways. However, the use of certain promoters may incur problems, such as being too strong. As a result, overexpression of a particular gene may occur and be detrimental to a cell. The cell's viability can thus be reduced and the production time may be limited.

The methods provided herein are utilized to provided a library of regulatory DNA constructs such as a library of modified promoters, a library of modified RBS and, a library of modified start codons, which may include stabilizing mRNA sequences to be introduced into bacterial host cells which results in a population of transformed cells having a range of gene expression. The range of gene expression is useful because it allows the selection of specific bacterial clones having an optimum level of expression but still maintaining cell viability (e.g. the flux production of the desired end product relative the viability of the host cell in sustaining the desired level of production or sustaining the desired level of production). In certain embodiments the optimum level of expression of a gene will be high and in other embodiments the optimum level of gene expression will be low. In one embodiment, the level of expression of a gene of interest in a clone library may range from −100 to +500%, also −50 to 150% and −80 to 100%. For example, the expression of a gene of interest in certain clones of a library may be 100% less than the expression of the gene in a corresponding parent. Also, the expression of the gene of interest in certain clones may be 500% greater than the expression of the same gene in the corresponding parent.

A direct advantage of this method is that a bacterial clone may be selected based on the expression level obtained from the DNA libraries and then be ready for use in a fermentation process whereby cell viability is not negatively affected by expression of the gene of interest.

The following Examples are for illustrative purposes only and are not intended, nor should they be construed as limiting the invention in any manner. Those skilled in the art will appreciate that variations and modifications can be made without violating the spirit or scope of the invention.

EXAMPLES

The *E. coli* strain MG1655 having ATCC No. 47076 was utilized to create a library of bacterial clones comprising a library of artificial promoters, a library of mRNA stabilizing sequences and a library of modified RBSs.

Example 1

Creation of a Library of *Escherichia coli* Clones with Different Levels of Expression of a Chromosomal Gene by Deleting a Regulator and Replacing the Natural Promoter by PCR Generated Artificial Promoters of Different Strength This example describes the deletion of lacI encoding a repressor and the replacement into the *Escherichia coli* genome of the natural lacZ (encoding the β-galactosidase) promoter by PCR generated artificial promoters of different strength.

a) Design of the Oligonucleotides for the lacZ Promoter Replacement.

Oligonucleotides (lacZF and degenerated lacZR) were designed to amplify by PCR a cassette containing an 79 bp sequence homologous to the 5' of the lacI gene, a chloramphenicol-resistance encoding gene (cat) flanked by baker yeast FRT sites, a library of three artificial GI promoter sequences (FIG. 6) and a 40 bp sequence homologous to the downstream region of the +1 transcription start site of the natural lacZ promoter.

The degenerated lacZR primers were 100 nucleotides long and included the entire sequence from the +1 of the transcription start site to the ATG of lacZ (365529 to 365567).

```
LacZR oligonucleotide:
                                  (SEQ ID NO. 57)
TAGCTGTTTCCTGTGTGAAATTGTTATCCGCTCACAATTAGTGGTTGAA

TTATTTGCTCAGGATGTGGCATHGTCAAGGGCATATGAATATCCTCCTT

AG
wherein H is A, C or T
```

The GI promoters from 4 bp upstream of the −35 to 8 bp downstream the −10, were degenerated at the last base of the −35 (TTGACA, TTGACT and TTGACG) to create the diversity. The priming site for pKD3 (Datsenko and Wanner, 2000) *PNAS*, 97: 6640-6645) an R6K plasmid containing the cat gene flanked by two FRT sites.

The lacZF primer is 100 nucleotides long (SEQ ID NO. 58) and contains: 79 bp of sequence (from 366734 to 366675) at the 5' end of the lacI gene and the priming site for pKD3

```
LacZF oligonucleotide:
                                  (SEQ ID NO. 58)
GTGAAACCAGTAACGTTATACGATGTCGCAGAGTATGCCGGTGTCTCTT

ATCAGACCGTTTCCCGCGTGGTGAACCAGGGTGTAGGCTGGAGCTGCTT

CG
``` b) Amplification and Purification of the GI Promoter Replacement Cassettes.

Primers lacZF and lacZR were used to amplify the library of promoter replacement cassettes using plasmid pKD3 as a template. The amplification used 30 cycles of 94° C. for 2 minutes; 60° C. for 30 sec; 72° C. for 2 min using Taq polymerase as directed by the manufacturer (BioLabs, New England). The mixture of 1.15 kb PCR products were gel purified using the Quiaquick gel extraction kit (QIAGEN, Inc.).

c) Creation of the Library of Clones with Different Artificial Promoter in from of the lacZ Genes.

Transformants carrying Red Helper plasmid (pKD 46) (Datsenko and Wanner, supra) were grown in 20 ml SOB medium with carbenicillin (100 mg/l) and L arabinose (10 mM) at 30° C. to an $OD_{550\ nm}$ of 0.6 and then made electrocompetent by concentration 100 fold and washed one time with ice water and twice with ice cold 10% glycerol. Electroporation was done using a Gene pulse (BioRad— model II apparatus 165-2106) with a voltage booster and 0.2 cm chamber according to manufactures instructions by using 50 µl of cells and 0.1 to 1.0 µg of the mixtures of purified PCR products (as described above). Shocked cells were added to 1 ml SOC medium incubated 2 hours at 30° C. and then half of the cells were spread on agar to select $Cm^R$ transformants. Xgal 40 mg/l was added on the agar plates to evaluate the β galactosidase expression. If cells did not grow within 24 hours, the remainder were spread after standing overnight at 30° C.

d) PCR Verification of the Transformants.

Mutants were grown overnight on LB medium with 30 mg/l Cm. 1 ml of culture was washed with ice cold water and the chromosomic DNA was recovered in the supernatant after heat treatment (5 min at 94° C.) of the washed cells. The PCR was performed using the chromosomic DNA and a set of two oligonucleotides (LacseqF and LacseqR). The amplification was performed as disclosed above. A 1.6 PCR product was obtained.

```
LacseqF oligonucleotide
GGCTGCGCAACTGTTGGGAA       (SEQ ID NO. 59)

LacseqR oligonucleotide
CATTGAACAGGCAGCGGAAAAG     (SEQ ID NO. 60)
```

The PCR product was digested by ECORV (1 U/µg of ECORV, 2 hrs at 37° C.). The comparison of the digestion profile of the mutants (modified precursor) with the wild-type strain showed that the ECORV is absent when the promoter is replaced.

The sequence of the $P_{GI}$ in the different clones was determined by sequencing the different 1.2 kb PCR products with the lacseqF primer. 50 µl of column purified PCR products (Quiaquick, Quiagen, Inc.) obtained from the chromosomic DNA of the mutants were used and sequenced by Genome Express (Meylan, France).

The organization of the GI lacZ promoter region in the three types of recombinant clones obtained is shown in FIG. 6. As expected, they only differ by one base pair in their −35 region and were named 1.6 GI lacZ for TTGACA, 1.5 GI lacZ for TTGACT and 1.20 GI lacZ for TTGACG.

e) β Galactosidase Activity

A 25 ml LB culture with Cm (30 mg/l) of the mutants was maintained for 5 hr at 37° C. The cells were centrifuged 10 min at 4000 g and resuspended in 300 μl of B-PER Bacterial Protein Extraction Reagent (Pierce, Rockford). After 10 min of incubation on ice, the solution was centrifuges 2 min at 12000 g at 4C to separate the soluble proteins from cell debris. The supernatant was used to evaluate the β galactosidase activity. The β galactosidase activity was measured using synthetic substrate ONPG (ortho-nitrophenyl β-D-galactopyranoside) according to the procedure of Miller, (1992) A SHORT COURSE IN BACTERIA GENETICS, Cold Spring Harbor Laboratory Press. The conditions of the reaction were, 37C, pH 7.3, λ 410 nm, light path 1 cm. (FIG. 7)

f) Elimination of the Antibiotic Resistance Gene:

pCP20 (Cherepanov et al., (1995) Gene: 158:9-14) is a plasmid that carries an ampicillin resistance marker, contains a temperature sensitive origin of replication and thermal induction of FLP synthesis. CmR mutants were transformed (pCP20) and ampicillin resistant transformants were selected at 30° C. A few colonies were purified selectively at 43° C. and then tested for loss of all antibiotic resistance. The majority lost the FRT flanked resistance gene and the FLP helper plasmid simultaneously.

Example 2

Creation of a Library of *Escherichia coli* Clones with Different Levels of Expression of a Chromosomal Gene by Replacing the Natural Promoter with the 1.6GI and Creating a Library of RBS with PCR Generated Linear DNA Fragments.

This example describes the deletion of lacI and the replacement into the *Escherichia coli* genome of the natural lacZ (encoding the β-galactosidase) promoters and RBS by a PCR generated artificial promoter and RBS with different binding capacities.

a) Design of the Oligonucleotides to Create a Library of Replacement Cassettes to Replace the Native Promoter and Modify the RBS and the Start Codon.

Oligonucleotide lacZRT was designed to amplify by PCR when used with lacZF a cassette containing a 79 bp sequence homologous to the 5' of the lacI gene, a chloroamphenicol resistance encoding gene (cat) flanked by baker yeast FRT sites, the 1.6GI promoter sequence (SEQ ID NO. 19) and a 40 bp sequence homologous to the downstream region of the +1 transcription start site of the natural lacZ promoter.

```
LacZRT oligonulceotide
                                            (SEQ ID NO. 70)
TAGCTGTTTCCTGTGTGAAATTGTTATCCGCTCACAATTAGTGGTTGAA

TTATTTGCTCAGGATGTGGCATGTCAAGGGCATATGAATATCCTCCTTA

G
```

A degenerate oligonucleotide, lacZRBSR, was designed with a 60 bases region homologous to lacZ after the start codon and a 40 bases region homologous to the lacZRT oligonucleotide. LacZRBS R oligonucleotide (SEQ ID NO. 61) CAGGGTTTTCCCAGTCACGACGTTGTAAAAC-GACGGCCAGTGAATCCGTAATCATGGTCATAG CTG-TYTYCTBYKWGAAATTGTTATCCGCTCACAATTA wherein B is T,C or G; K is T or G; Y is C or T; and W is A or T.

This oligonucleotide (SEQ ID NO. 61) is degenerated in the RBS sequence (AAGGAGGAAA, degeneration of the $1^{st}$ base (A) by a T, $2^{nd}$ base (A) by a C; $3^{rd}$ base (G) by a A; 4th base (G) by an A or C; $7^{th}$ base (G) by an A and the 9th base (A) by a G.

b) Amplification and Purification of the Replacement Cassettes.

Primers lacZF and lacZRT were used to amplify by PCR the 1.6 GI promoter replacement cassette using pKD3 as template DNA. The amplification used 30 cycles of 94° C. for 2 minutes; 60° C. for 30 sec; 72° C. for 2 min using Taq polymerase as directed by the manufacturer (BioLabs, New England).

The lacZF and lacZRBSR primers were the used to amplify the library of replacement constructs using the 1.6GI promoter replacement cassette created above as a template. The amplification used 30 cycles of 94° C. for 2 minutes; 60° C. for 3 sec; 72° C. for 2 min using Taq polymerase as directed by the manufacturer (BioLabs, New England). The 1.15 kb PCR products were gel purified using the Quiaquick gel extraction kit (QIAGEN, Inc.).

c) Creation of a Library of lacZ Expression Levels in *Escherichia coli* by Homologous Recombination in the Chromosome using Replacement Cassettes in the Form of Linear DNA.

Transformants carrying red helper plasmid (pKD 46) (Datsenko and Wanner, supra) were grown in 20 ml SOB medium with carbenicillin (100 mg/l) and L arabinose (10 mM) at 30° C. to an $OD_{550\ nm}$ of 0.6 and then made electrocompetent by concentration 100 fold and washed one time with ice water and twice with ice cold 10% glycerol. Electroporation was done using a Gene pulse (BioRad—model II apparatus 165-2106) according to manufactures instructions by using 50 μl of cells and 0.1 0 1.0 μg of the mixtures of purified PCR products (as described above). Shocked cells were added to 1 ml SOC medium incubated 2 hours at 30° C. and then half of the cells were spread on agar to select CmR transformants. Xgal 40 mg/l was added on the agar plates to evaluate the β galactosidase expression. If cells did not grow within 24 hours, the remainder were spread after standing overnight at 30° C.

d) PCR Verification of the Transformants.

Mutants were grown overnight on LB medium with 30 mg/l Cm. 1.0 ml of culture was washed with ice cold water and the chromosomic DNA was recovered in the supernatant after heat treatment (5 min at 94° C.) of the washed cells. The PCR was performed using the chromosomic DNA and the two oligonucleotides, LacseqF and LacseqR as disclosed above in example 1. Amplification also followed the protocol of example 1. A 1.6 kb PCR product was obtained. The PCR product was digested by ECORV (1 U/μg of ECORV, 2 hrs at 37° C.). The comparison of the digestion profile of the mutants with the wild-type strain showed that the ECORV site is absent when the promoter is replaced.

The sequence of the replacement cassette in the different clones was determined by sequencing the different 1.6 kb PCR products with the lacFprimer. 50 μl of column-purified PCR products (Quiaquick, Quiagen, Inc.) obtained from the chromosomic DNA of the mutants were used and sequenced by Genome Express (Meylan, France).

Eight of the recombinant clones were designated as indicated below and the organization of the upstream region of lacZ in each recombinant clone is A=CAAGGAGGAA ACAGCTATG (SEQ ID NO.22), B=CAAGAAGGAA ACAGCTATG (SEQ ID NO. 23), C=CACACAGGAA ACAGCTATG (SEQ ID NO. 24), D=CTCACAGGAG ACAGCTATG (SEQ ID NO. 25), E=CTCACAGGAA ACAGCTATG (SEQ ID NO. 26), F=CACACAGAAA ACAGCTATG (SEQ ID NO. 27), G=CTCACAGAGA ACAGCTATG (SEQ ID NO. 28), and H=CTCACAGAAA ACAGCTATG (SEQ ID NO. 29).

As expected the transformants differed only by RBS and the range of expression among the different clones of the library was from 5.7 to 0.02 U/mg of protein (FIG. 8).

Elimination of the antibiotic resistance gene was performed as disclosed in example 1.

Example 3

Creation of a Library of *Escherichia coli* Clones with Different Levels of Expression of a Chromosomal Gene by both Replacing the Native Promoter by the 1.6 GI Promoter and Introducing mRNA Stabilizing Structures using a Library of PCR Generated Linear DNA Ffragments This example describes the deletion of lacI and the replacement into the *Escherichia coli* genome of the natural lacZ (encoding the β-galactosidase) promoter and the lac operator by PCR generated artificial promoters of different strength and artificial mRNA stabilizing structures with different efficiencies.

a) Design of the Oligonucleotides to Create a Library of Replacement Cassettes to Replace the Promoter and the lac Operator by a Library of Artificial Promoters and mRNA Stabilizing Structures.

To generate broader lacZ expression level, a library of replacement cassettes was designed to remove lacI, the natural lacZ promoter and the lac operator and replace them by the 1.6 GI promoter and a library of mRNA stabilizing structure. For this purpose, a degenerate oligonucleotide, lacZMRNA, was designed with a 43 base region homologous to lacZ downstream the RBS site, 34 bases of mRNA stabilizing structure and a 23 bases region homologous to the lacZRT oligonucleotide upstream the +1 of transcription. This oligonucleotide is degenerated in the mRNA stabilizing sequence.

LacZmRNA R oligonucleotide (SEQ ID NO. 62)
CGACGGCCAGTGAATCCGTAATCATGGTCATAGCT GTTTCCTCCTTCGTCAACAATATCTCACT CGAGATAASTCGASSTAGTGGTTGAATTATTTGCTCAGG, wherein S is C or G.

If lacF and lacMRNA are used in a PCR reaction with the promoter replacement cassette (generated by PCR using the primers lacZF and lacZRT (SEQ ID NO. 70) as template DNA, a new library will be obtained with lacI deleted, the promoter replaced and the mRNA stabilizing structure introduced.

b) Amplification and Purification of the Replacement Cassettes:

Primers lacF and lacZMRNA were used to amplify the library of replacement cassettes using the 1.6 GI promoter replacement cassette created in example 2 as template DNA. Amplification followed the procedures of example 1. The 1.15 kb PCR products were purified by agarose gel electrophoresis followed by QIAquick gel extraction Kit (QIAGEN).

c) Creation of a Library of lacZ Expression Level in *Escherichia coli* by Homologous Recombination in the Chromosome using Replacement Cassettes in the Form of Linear DNA:

Transformants carrying Red Helper plasmid (pKD 46) (Datsenko and Wanner, supra) were grown in 20 ml SOB medium with carbenicillin (100 mg/l) and L arabinose (10 mM) at 30° C. to an $OD_{550\ nm}$ of 0.6 and then made electrocompetent by concentration 100 fold and washed one time with ice water and twice with ice cold 10% glycerol. Electroporation was done using a Gene pulse (BioRad— model II apparatus 165-2106) with a voltage booster and 0.2 cm chambers according to manufactures instructions by using 50 µl of cells and 0.1 to 1.0 µg of the purified PCR products (as described in b) above). Shocked cells were added to 1 ml SOC medium incubated 2 hours at 30° C. and then half of the cells were spread on agar to select $Cm^R$ transformants. Xgal 40 mg/l was added on the agar plates to evaluate the β galactosidase expression. If cells did not grow within 24 hours, the remainder were spread after standing overnight at 30° C.

d) PCR Verification of the Transformants.

Mutants were grown overnight on LB medium with 30 mg/l Cm. 1.0 ml of culture was washed with ice cold water and the chromosomic DNA was recovered in the supernatant after heat treatment (5 min at 94° C.) of the washed cells.

The PCR was performed using the chromosomic DNA and a set of two oligonucleotides, LacseqF and LacseqR as disclosed above in example 1. Amplification also followed the protocol of example 1. A 1.6 kb PCR product was obtained. The PCR product was digested by ECORV (1 U/µg ECORV, 2 hrs at 37° C.). The comparison of the digestion profile of the mutants with the wild-type strain showed that the ECORV site is absent when the promoter is replaced.

The sequence of the replacement cassette in the different clones was determined by sequencing the different 1.6 kb PCR products with the lacFprimer. 50 µl of column-purified PCR products (Quiaquick, Quiagen, Inc.) obtained from the chromosomic DNA of the mutants were used and sequenced by Genome Express (Meylan, France).

The organization of the upstream region of lacZ of the recombinant clones is shown in FIG. 9. As expected the range of expression among the different clones of the library was from 4.1 to 18.4 U/mg protein.

Example 4

Creation of a Library of *Escherichia coli* Clones with Different Artificial Promoters, Modified start Codons and Modified RBS using a Library of PCR Generated linear DNA Fragments This example describes the deletion of lacI and the replacement into the *Escherichia coli* genome of the natural lacZ (encoding the β-galactosidase) promoter, RBS and start codon by PCR generated artificial promoters of different strength, RBS with different binding capacity and start codons of different efficiency.

a) Design of the Oligonucleotides for the lacZ Promoter Replacement.

To generate broader lacZ expression level, a library of replacement cassettes was designed to remove lacI, replace the promoter and modify the RBS. A degenerate oligonucleotide in RBS and in the start codon, lacZRBSR2 was designed with a 60 base region homologous to lacZ after the start codon and a 40 base region homologous to the lacR oligonucleotide.

LacZRBS R2 oligonucleotide (SEQ ID NO. 71)
CAGGGTTTTCCCAGTCACGACGTTGTAAAAC-
GACGGCCAGTGAATCCGTAATCATGGTCAHAG
CTGTYTYCTBYKWGAAATTGTTATCCGCTCA-
CAATTA wherein B is T,C or G; H is A, T or C; K is T or G; Y is C or T; and W is A or T.

b) Amplification and Purification of the $P_{GI}$ Replacement Cassettes.

Primers lacZF and lacZR were used to amplify the library of promoter replacement cassettes using plasmid pKD3 as a template as described in example 1. Primers LacZF and LacZRSB2R were used to amplify the library of promoter replacement cassettes with a modified start codon and a modified RBS using the mixture of PCR products obtained above as a template. Amplification followed the procedures of example 1. The 1.15 kb PCR products were purified by agarose gel electrophoresis followed by QIAquick gel extraction Kit (QIAGEN).

c) Creation of the Library of Clones with Different Artificial Promoters with Modified start Codons and Modified RBS in front of the lacZ Genes.

Transformants carrying Red Helper plasmid (pKD 46) (Datsenko and Wanner, supra) were grown in 20 ml SOB medium with carbenicillin (100 mg/l) and L arabinose (10 mM) at 30° C. to an $OD_{550\ nm}$ of 0.6 and then made electrocompetent by concentration 100 fold and washed one time with ice water and twice with ice cold 10% glycerol. Electroporation was done using a Gene pulse (BioRad—model II apparatus 165-2106) with a voltage booster and 0.2 cm chambers according to manufactures instructions by using 50 µl of cells and 0.1 to 1.0 µg of the purified PCR products (as described above). Shocked cells were added to 1 ml SOC medium incubated 2 hours at 30° C. and then half of the cells were spread on agar to select $Cm^R$ transformants. Xgal 40 mg/l was added on the agar plates to evaluate the β galactosidase expression. If cells did not grow within 24 hours, the remainder were spread after standing overnight at 30° C.

d) PCR Verification of the Transformants.

Mutants were grown overnight on LB medium with 30 mg/l Cm. 1.0 ml of culture was washed with ice cold water and the chromosomic DNA was recovered in the supernatant after heat treatment (5 min at 94° C.) of the washed cells.

The PCR was performed using the chromosomic DNA and a set of two oligonucleotides, LacseqF and LacseqR as disclosed above in example 1. Amplification also followed the protocol of example 1. A 1.6 kb PCR product was obtained. The PCR product was digested by ECORV (1 U/µg of ECORV, 2 hrs at 37C). The comparison of the digestion profile of the mutants with the wild-type strain showed that the ECORV site disappeared with the promoter replacement.

The sequence of the GI promoter in the different clones was determined by sequencing the different PCR products with the lacseqFprimer. 50 µl of column-purified PCR products (Quiaquick, Quiagen, Inc.) obtained from the chromosomic DNA of the mutants were used and sequenced by Genome Express (Meylan, France). The organization of the upstream region of lacZ in four of the recombinant clones obtained was as expected.

1.6GI-clone 1: start codon-TTG; RBS-TCACAGGAGA; β-galactosidase activity, 0.28 U/mg;
1.6GI-clone 2: start codon-ATG; RBS-AAGGAGGAA; β-galactosidase activity, 5.7 U/mg;
1.2GI-clone 3: start codon-ATG; RBS-ACACAGGAAA; β-galactosidase activity, 0.68 U/mg; and
1.6GI-clone 4: start codon-TTG; RBS-ACACAGAAGA; β-galactosidase activity, 0.032 U/mg.

Those skilled in the art will recognize or be able to ascertain using not more than routine experimentation, many equivalents to the specific embodiments of the invention described herein. Such equivalents are intended to be encompassed by the following claims.

SEQUENCE LISTING

The sequence listing submitted via EFS on Jun. 7, 2011, in compliance with 37 C.F.R. §1.52(e), is incorporated herein by reference. The sequence listing text file submitted via EFS contains the file "743_2_US seqlist.txt", created on Jun. 6, 2011, which is 15,857 bytes in size.

The invention claimed is:

1. A method of creating a library of artificial bacterial promoters comprising:
   a) obtaining an insertion DNA cassette, wherein the DNA cassette comprises a sense strand having a first end (5') and a second end (3'), an antisense strand having a first end (5') and a second end (3'), wherein the DNA cassette comprises a first recombinase site, a second recombinase site and a marker gene located between the first and the second recombinase sites;
   b) obtaining a first oligonucleotide which comprises in sequential order from the 5' end,
      i) a first nucleic acid fragment comprising a nucleic acid sequence homologous to a segment upstream of the −35 consensus sequence of a promoter of a bacterial chromosomal gene of interest, and
      ii) a second nucleic acid fragment comprising a first primer site that is homologous to the first (5') end of the sense strand of the insertion DNA cassette;
   c) obtaining a second oligonucleotide which comprises in sequential order from the 3' end,
      i) a third nucleic acid fragment comprising a second primer site that is homologous to the first (5') end of antisense strand of the insertion DNA cassette,
      ii) an artificial bacterial precursor promoter comprising a −35 consensus region (−35 to −30), a linker sequence and a −10 consensus region (−12 to −7), wherein the linker sequence comprises between 14-20 nucleotides and is flanked by the −35 consensus region and the −10 consensus region, wherein the artificial bacterial precursor promoter comprises at least one degenerated nucleotide position of the −35 consensus region, the −10 consensus region or the linker sequence, and wherein the −35 consensus region and the −10 consensus region of the artificial bacterial promoter each include between 4 to 6 conserved nucleotides of the precursor bacterial promoter, and iii) a fourth nucleic acid fragment comprising a nucleic acid sequence homologous to a region downstream of the transcription start site of the promoter of the bacterial chromosomal gene of interest, d) mixing the first oligonucleotide, the second oligonucleotide and the DNA cassette, and e) performing a polymerase chain reaction (PCR) on the mixture of (d) to obtain a library of double stranded amplified products comprising artificial bacterial promoters.

2. The method according to claim 1 further comprising purifying the amplified products.

3. The method according to claim 1, wherein the −35 consensus region of the precursor bacterial promoter is selected from the group consisting of TTGACA, TTGCTA, TTGCTT, TTGATA, TTGACT, TTTACA and TTCAAA.

4. The method according to claim 1, wherein the −35 consensus region of the precursor bacterial promoter comprises a modification to the −30 residue of the precursor promoter.

5. The method according to claim 1, wherein the −10 consensus region of the precursor bacterial promoter is selected from the group consisting of TAAGAT, TATAAT, AATAAT, TATACT, GATACT, TACGAT, TATGTT and GACAAT.

6. The method according to claim 1, wherein the −35 consensus region of the precursor bacterial promoter is TTGACA and the −10 consensus region of the precursor promoter is TATAAT.

7. The method according to claim 1, wherein the −35 consensus region of the precursor bacterial promoter is TTGACA and the −10 consensus region of the precursor is AATAAT.

8. The method according to claim 1, wherein the linker sequence comprises between 16 and 18 nucleotides.

9. The method according to claim 1, wherein the precursor bacterial promoter is obtained from a promoter selected from the group consisting of $P_{trc}$ (SEQ ID NO 2); $P_{D/E20}$ ((SEQ ID NO. 4); $P_{H207}$ (SEQ ID NO. 3); $P_{N25}$ (SEQ ID NO. 5); $P_{G25}$ (SEQ ID NO. 6); $P_{J5}$ (SEQ ID NO. 7); $P_{A1}$ (SEQ ID NO. 8); $P_{A2}$(SEQ ID NO. 9); $P_{A3}$ (SEQ ID NO. 10); $P_{lac}$ (SEQ ID NO. 1); $P_{GI}$ (SEQ ID NO. 15); $P_{lacUV5}$ (SEQ ID NO. 12); $P_{CON}$ (SEQ ID NO. 4); and $P_{bls}$ (SEQ ID NO. 14).

10. The method according to claim 1, wherein the library of artificial bacterial promoters includes SEQ ID NO:15, SEQ ID NO:16 and SEQ ID NO:17.

11. The method according to claim 1, wherein the precursor bacterial promoter and the bacterial chromosomal gene of interest are heterologous.

12. The method according to claim 1, wherein the precursor bacterial promoter and the bacterial chromosomal gene of interest are homologous.

13. The method according to claim 1, further comprising:

f) obtaining a third oligonucleotide which comprises in sequential order from the 5' end,
   i) a fifth nucleic acid fragment comprising a nucleic acid sequence homologous to a region downstream of the transcription start site of the promoter of the bacterial chromosomal gene of interest,
   ii) a modified ribosome binding site of the bacterial chromosomal gene of interest, the ribosome binding site including at least one modified nucleotide, and
   iii) a sixth nucleic acid fragment comprising a third primer site that is homologous to a downstream region of the −10 consensus region of the second oligonucleotide, g) mixing the double stranded amplified products of (e) with the third oligonucleotide and the first oligonucleotide, and h) performing a PCR on the mixture of (g) to obtain PCR products comprising artificial bacterial promoters with modified ribosome binding sites.

14. The method according to claim 13, wherein the ribosome binding site from the precursor bacterial promoter is selected from the group consisting of AGGAAA, (SEQ ID NO. 30), AGAAAA (SEQ ID NO. 31), AGAAGA (SEQ ID NO. 32), AGGAGA (SEQ ID NO. 33), AAGAAGGAAA (SEQ ID NO. 34), AAGGAAAA (SEQ ID NO. 35), AAGGAAAG (SEQ ID NO. 36), AAGGAAAU (SEQ ID NO. 37), AAGGAAAAA (SEQ ID NO. 38), AAGGAAAAG (SEQ ID NO. 39), AAGGAAAAU (SEQ ID NO. 40), AAGGAAAAAA (SEQ ID NO. 41), AAGGAAAAAG (SEQ ID NO. 42), AAGGAAAAAU (SEQ ID NO. 43), AAGGAAAAAAA (SEQ ID NO. 44), AAGGAAAAAAG (SEQ ID NO. 45), AAGGAAAAAAU (SEQ ID NO. 46), AAGGAAAAAAAA (SEQ ID NO. 47), AAGGAAAAAAAG (SEQ ID NO. 48), AAGGAAAAAAAU (SEQ ID NO. 49), AAGGAAAAAAAAA (SEQ ID NO. 50), AAGGAAAAAAAAG (SEQ ID NO. 51), AAGGAAAAAAAAU (SEQ ID NO. 52), AAGGAAAAAAAAAA (SEQ ID NO. 53), AAGGAAAAAAAAAG (SEQ ID NO. 54), AAGGAGGAAA (SEQ ID NO. 55), and AAGGAAAAAAAAAU (SEQ ID NO. 56).

15. The method according to claim 13, wherein the third oligonucleotide further comprises a stabilizing mRNA sequence between the modified ribosome binding site and the sixth nucleic acid fragment.

16. The method of claim 13, wherein the third oligonucleotide further comprises a modified start codon, which may be a modified start codon of the bacterial chromosomal gene of interest.

17. The method according to claim 1 further comprising, j) obtaining a third oligonucleotide comprising in sequential order from the 5' end,
   i) a fifth nucleic acid fragment comprising a nucleic acid sequence homologous to a region downstream of the transcription start site of the promoter of the bacterial chromosomal gene of interest,
   ii) a start codon of the bacterial chromosomal gene of interest, wherein the start codon is degenerated and includes at least one modified nucleotide, and
   iii) a sixth nucleic acid fragment comprising a third primer site that is homologous to the downstream region of the −10 consensus region of the second oligonucleotide, k) mixing the PCR products of (e) with the third oligonucleotide and the first oligonucleotide, and l) performing a PCR on the mixture of k) to obtain PCR products comprising artificial bacterial promoters with modified start codons.

18. The method according to claim 17, wherein the third oligonucleotide further comprises a stabilizing mRNA sequence between the start codon and the sixth nucleic acid fragment.

19. A method of modifying a promoter in bacterial host cells comprising:

a) obtaining a library of double stranded amplified products comprising artificial bacterial promoters according to claim 1;

b) transforming bacterial host cells with the library, wherein the double stranded amplified products comprising the artificial bacterial promoters are integrated into the bacterial host cells by homologous recombination to produce transformed bacterial cells;

c) growing the transformed bacterial cells;

d) selecting the transformed bacterial cells comprising the artificial bacterial promoters.

20. A method of modifying a promoter in bacterial host cells comprising:

a) obtaining a library of double stranded amplified products comprising artificial bacterial promoters according to claim 13;

b) transforming bacterial host cells with the library, wherein the double stranded amplified products comprising the artificial bacterial promoters are integrated into the bacterial host cells by homologous recombination to produce transformed bacterial cells;

c) growing the transformed bacterial cells;

d) selecting the transformed bacterial cells comprising at least one artificial bacterial promoter.

21. A method of modifying a promoter in bacterial host cells comprising:

a) obtaining a library of double stranded amplified products comprising artificial bacterial promoters according to claim 17;

b) transforming bacterial host cells with the library, wherein the double stranded amplified products comprising the artificial bacterial promoters are integrated into the bacterial host cells by homologous recombination to produce transformed bacterial cells;

c) growing the transformed bacterial cells;

d) selecting the transformed bacterial cells comprising at least one artificial bacterial promoter.

22. The method according to claim 19, wherein the bacterial host cell is selected from the group consisting of *E. coli, Pantoea* sp. and *Bacillus* sp.

23. The method according to claim 20, wherein the bacterial host cell is selected from the group consisting of *E. coli, Pantoea* sp. and *Bacillus* sp.

24. The method according to claim 21, wherein the bacterial host is selected from the group consisting of *E. coli, Pantoea* sp. and *Bacillus* sp.

25. A method of creating a library of bacterial cells having a range of expression levels of a chromosomal gene of interest comprising, a) obtaining a library of double stranded polynucleotides comprising artificial bacterial promoters according to claim 1;

b) transforming bacterial host cells with the double stranded polynucleotides, wherein the double stranded polynucleotides comprising the artificial bacterial promoters are integrated into bacterial host cells by homologous recombination to produce transformed bacterial cells; and c) growing the transformed bacterial cells to obtain a library of transformed bacterial cells, wherein the transformed bacterial cells in the library exhibit a range of expression levels of a chromosomal gene of interest.

26. The method according to claim 25, further comprising selecting transformed bacterial cells from the library.

27. The method of claim 26, wherein the selected transformed bacterial cells have a low level of expression of the gene of interest.

28. The method of claim 26, wherein the selected transformed bacterial cells have a high level of expression of the gene of interest.

29. The method according to claim 26 further comprising excising the marker gene from the transformed bacterial cells.

30. The method according to claim 26, wherein the bacterial host cell is an *E. coli, Bacillus* sp. or *Pantoea* sp. cell.

* * * * *